(12) United States Patent
Srivastava et al.

(10) Patent No.: US 10,463,649 B2
(45) Date of Patent: Nov. 5, 2019

(54) INHIBITORS OF MC1-1 AS DRUGS TO OVERCOME RESISTANCE TO BRAF INHIBITORS AND MEK INHIBITORS

(71) Applicant: Texas Tech University System, Lubbock, TX (US)

(72) Inventors: Sanjay K. Srivastava, Amarillo, TX (US); Neel M. Fofaria, Amarillo, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 15/580,991

(22) PCT Filed: Jun. 6, 2016

(86) PCT No.: PCT/US2016/036002
§ 371 (c)(1),
(2) Date: Dec. 8, 2017

(87) PCT Pub. No.: WO2016/200726
PCT Pub. Date: Dec. 15, 2016

(65) Prior Publication Data
US 2018/0161313 A1 Jun. 14, 2018

Related U.S. Application Data

(60) Provisional application No. 62/172,327, filed on Jun. 8, 2015.

(51) Int. Cl.
| | |
|---|---|
| *C07D 209/08* | (2006.01) |
| *C07D 209/42* | (2006.01) |
| *C07D 211/34* | (2006.01) |
| *C07D 215/48* | (2006.01) |
| *C07D 217/06* | (2006.01) |
| *A61K 31/4184* | (2006.01) |
| *A61K 31/445* | (2006.01) |
| *A61K 45/06* | (2006.01) |
| *A61K 31/165* | (2006.01) |
| *A61K 31/167* | (2006.01) |
| *A61K 31/40* | (2006.01) |

(Continued)

(52) U.S. Cl.
CPC ........ *A61K 31/4184* (2013.01); *A61K 31/165* (2013.01); *A61K 31/167* (2013.01); *A61K 31/341* (2013.01); *A61K 31/40* (2013.01); *A61K 31/405* (2013.01); *A61K 31/4025* (2013.01); *A61K 31/4164* (2013.01); *A61K 31/4178* (2013.01); *A61K 31/4196* (2013.01); *A61K 31/423* (2013.01); *A61K 31/4245* (2013.01); *A61K 31/433* (2013.01); *A61K 31/437* (2013.01); *A61K 31/444* (2013.01); *A61K 31/445* (2013.01); *A61K 31/4436* (2013.01); *A61K 31/4439* (2013.01); *A61K 31/4525* (2013.01); *A61K 31/47* (2013.01); *A61K 31/4709* (2013.01); *A61K 31/495* (2013.01); *A61K 31/496* (2013.01); *A61K 31/4965* (2013.01); *A61K 31/50* (2013.01); *A61K 31/501* (2013.01); *A61K 31/506* (2013.01); *A61K 31/519* (2013.01); *A61K 31/538* (2013.01); *A61K 31/5375* (2013.01); *A61K 31/5377* (2013.01); *A61K 31/54* (2013.01); *A61K 31/541* (2013.01); *A61K 31/5415* (2013.01); *A61K 45/06* (2013.01); *A61P 35/00* (2018.01); *C07C 233/87* (2013.01); *C07C 237/00* (2013.01); *C07C 237/52* (2013.01); *C07D 207/337* (2013.01); *C07D 209/08* (2013.01); *C07D 209/42* (2013.01); *C07D 211/34* (2013.01); *C07D 215/48* (2013.01); *C07D 217/06* (2013.01); *C07D 233/60* (2013.01); *C07D 235/10* (2013.01); *C07D 235/12* (2013.01); *C07D 235/16* (2013.01); *C07D 235/28* (2013.01); *C07D 249/12* (2013.01); *C07D 263/34* (2013.01); *C07D 265/36* (2013.01); *C07D 279/02* (2013.01); *C07D 295/108* (2013.01); *C07D 307/54* (2013.01); *C07D 317/60* (2013.01); *C07D 401/06* (2013.01); *C07D 403/06* (2013.01); *C07D 403/14* (2013.01); *C07D 405/06* (2013.01); *C07D 409/14* (2013.01); *C07D 413/06* (2013.01); *C07D 417/12* (2013.01); *C07D 487/04* (2013.01); *G01N 33/5011* (2013.01); *G01N 2333/4703* (2013.01)

(58) Field of Classification Search
CPC .. C07D 209/08; C07D 211/34; C07D 215/48; C07D 217/06
See application file for complete search history.

(56) References Cited

U.S. PATENT DOCUMENTS

| | | | |
|---|---|---|---|
| 8,853,209 | B2 | 10/2014 | Song et al. |
| 9,035,047 | B2 | 5/2015 | Wang et al. |

(Continued)

FOREIGN PATENT DOCUMENTS

| | | |
|---|---|---|
| WO | 2007097470 A2 | 8/2007 |
| WO | 2008005266 A2 | 1/2008 |

(Continued)

OTHER PUBLICATIONS

Wu, et al. Document No. 151:492, retrieved from STN; (2009).*

(Continued)

*Primary Examiner* — Shawquia Jackson
(74) *Attorney, Agent, or Firm* — Edwin S. Flores; Daniel J. Chalker; Chalker Flores, LLP

(57) ABSTRACT

The present invention includes compositions and methods for inhibiting MCL-1, including novel inhibitors of MCL-1, and compositions and methods for treating a subject with cancer that is refractory to one or more MAPK pathway protein inhibitors.

9 Claims, 9 Drawing Sheets

(51) Int. Cl.
| | |
|---|---|
| *A61K 31/4025* | (2006.01) |
| *A61K 31/4164* | (2006.01) |
| *A61K 31/4196* | (2006.01) |
| *A61K 31/433* | (2006.01) |
| *A61K 31/4436* | (2006.01) |
| *A61K 31/47* | (2006.01) |
| *A61K 31/4709* | (2006.01) |
| *A61K 31/495* | (2006.01) |
| *A61K 31/496* | (2006.01) |
| *A61K 31/50* | (2006.01) |
| *A61K 31/519* | (2006.01) |
| *A61K 31/5375* | (2006.01) |
| *A61K 31/538* | (2006.01) |
| *A61K 31/54* | (2006.01) |
| *C07D 317/60* | (2006.01) |
| *C07D 233/60* | (2006.01) |
| *C07D 401/06* | (2006.01) |
| *C07D 235/10* | (2006.01) |
| *C07D 235/12* | (2006.01) |
| *C07D 235/16* | (2006.01) |
| *C07D 235/28* | (2006.01) |
| *C07D 403/06* | (2006.01) |
| *C07D 403/14* | (2006.01) |
| *C07D 405/06* | (2006.01) |
| *C07D 409/14* | (2006.01) |
| *C07D 413/06* | (2006.01) |
| *C07D 417/12* | (2006.01) |
| *C07D 249/12* | (2006.01) |
| *C07D 487/04* | (2006.01) |
| *C07D 263/34* | (2006.01) |
| *C07C 237/00* | (2006.01) |
| *C07D 265/36* | (2006.01) |
| *C07D 207/337* | (2006.01) |
| *C07D 279/02* | (2006.01) |
| *C07D 295/108* | (2006.01) |
| *C07D 307/54* | (2006.01) |
| *C07C 233/87* | (2006.01) |
| *C07C 237/52* | (2006.01) |
| *A61P 35/00* | (2006.01) |
| *A61K 31/341* | (2006.01) |
| *A61K 31/405* | (2006.01) |
| *A61K 31/4178* | (2006.01) |
| *A61K 31/423* | (2006.01) |
| *A61K 31/4245* | (2006.01) |
| *A61K 31/437* | (2006.01) |
| *A61K 31/4439* | (2006.01) |
| *A61K 31/444* | (2006.01) |
| *A61K 31/4525* | (2006.01) |
| *A61K 31/4965* | (2006.01) |
| *A61K 31/501* | (2006.01) |
| *A61K 31/506* | (2006.01) |
| *A61K 31/5377* | (2006.01) |
| *A61K 31/541* | (2006.01) |
| *A61K 31/5415* | (2006.01) |
| *G01N 33/50* | (2006.01) |

(56) References Cited

U.S. PATENT DOCUMENTS

2013/0035304 A1   2/2013   Walensky et al.
2015/0045357 A1   2/2015   Nikolovska-Coleska et al.

FOREIGN PATENT DOCUMENTS

WO   2014144130 A2   9/2014
WO   2014152588 A1   9/2014

OTHER PUBLICATIONS

Pothier, et al. Document No. 157:295015, retrieved from STN; (2012).*
Goldfarb, et al. Document No. 151:92838, retrieved from STN; (2009).*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Fofaria, Neel M. et al. "Overexpression of Mcl-1 confers resistance to BRAF (V600E) inhibitors alone and in combination with MEK1/2 inhibitors in melanoma" Oncotarget, Oct. 14, 2015, vol. 6, No. 38, pp. 40535-40556.
International Preliminary Report on Patentability (PCT/US2016/036002) dated Dec. 21, 2017.
International Search Report and Written Opinion (PCT/US2016/036002) dated Aug. 25, 2016.

* cited by examiner

Figure 7
A
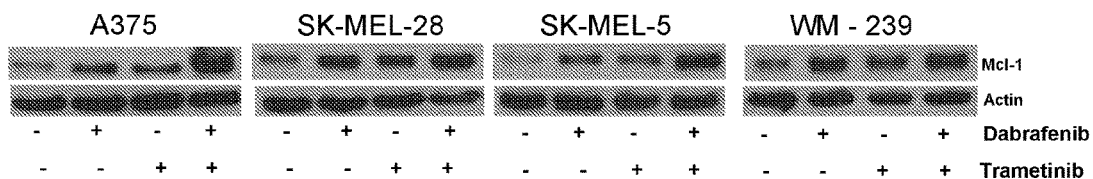
B
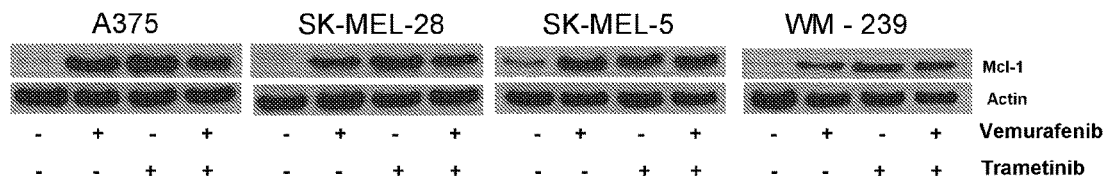
C
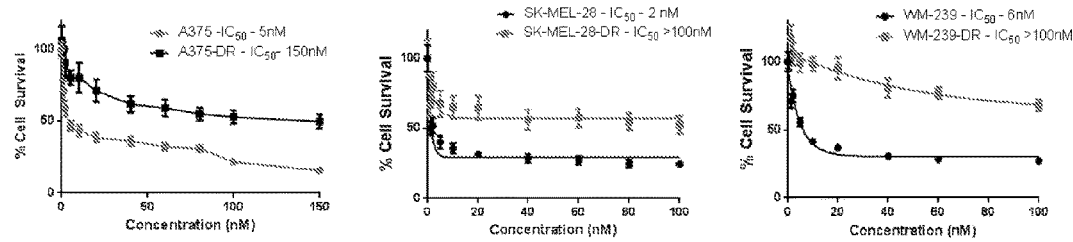
D
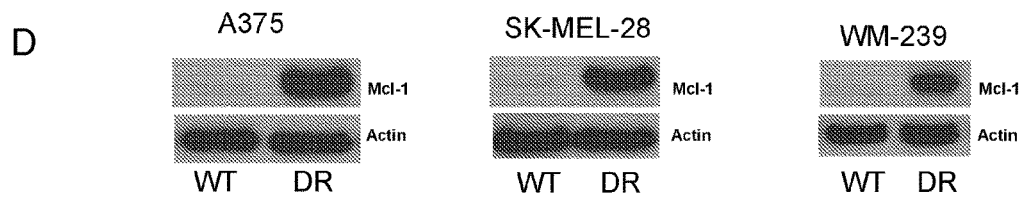

A 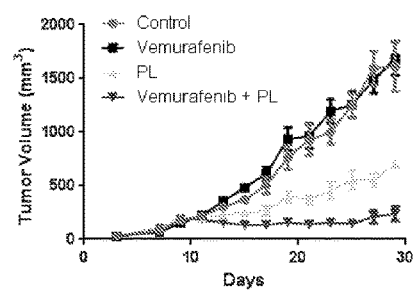
B 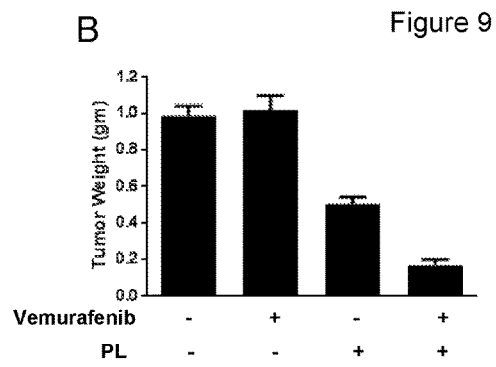
Figure 9
C SK-MEL-28 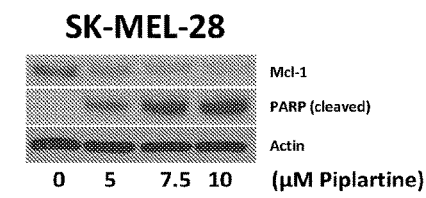
D SK-MEL-2 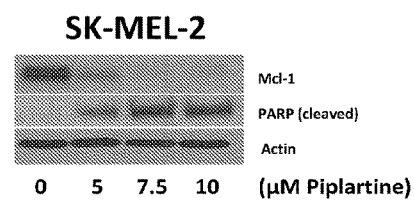

INHIBITORS OF MC1-1 AS DRUGS TO OVERCOME RESISTANCE TO BRAF INHIBITORS AND MEK INHIBITORS

CROSS-REFERENCE TO RELATED APPLICATIONS

This application is the National Stage of International Application No. PCT/US2016/036002, filed on Jun. 6, 2016, which claims priority to U.S. Provisional Patent Application Ser. No. 62/172,327, filed on Jun. 8, 2015. The contents of both applications are incorporated by reference herein in their entirety.

STATEMENT OF FEDERALLY FUNDED RESEARCH

This invention was made with U.S. Government support awarded by NSF grant number 1150836. The government has certain rights in this invention.

TECHNICAL FIELD OF THE INVENTION

The present invention relates in general to the field of cancer therapy, and more particularly, to novel compositions and methods that overcome resistance to B-Raf (BRAF) and Mitogen-activated protein kinase (MEK) inhibitors.

BACKGROUND OF THE INVENTION

Without limiting the scope of the invention, its background is described in connection with cancer treatments related to McL-1.

U.S. Pat. No. 9,035,047, issued to Wang, et al., is entitled "7-substituted indole Mcl-1 inhibitors", which are compounds said to inhibit the activity of anti-apoptotic Mcl-1 protein, compositions containing the compounds, and methods of treating diseases involving overexpressed or unregulated Mcl-1 protein.

U.S. Pat. No. 8,853,209, issued to Song, et al., entitled, "1-oxyalkyl-2-carboxy-7-nonsubstituted indole derivatives", which has the formula:

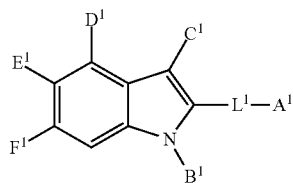

which is said to inhibit the activity of anti-apoptotic Mcl-1 protein, compositions containing the compounds, and methods of treating diseases involving overexpressed or unregulated Mdl-1 protein, such as leukemia and lymphoma.

United States Patent Application Publication No. 20150045357, filed by Nikolovska-Coleska, et al., entitled "Small Molecule Inhibitors of MCL-1 and Uses Thereof" is said to teach a new class of small-molecules having a [(1-Piperazinyl)-4-pyridinylmethyl]-Naphtho[1,2-b]furan structure which function as inhibitors of Mcl-1 protein, and their use as therapeutics for the treatment of cancer and other diseases.

United States Patent Application Publication No. 20130035304, filed by Walensky, et al., entitled "Small Molecules for the Modulation of McL-1 and Methods of Modulating Cell Death, Cell Division, Cell Differentiation And Methods of Treating Disorders" is said to relate to compounds which selectively bind to the survival protein McL-1 with high affinity and selectivity, pharmaceutical compositions containing such compounds and the use of those compounds or compositions for modulating McL-1 activity and for treating hyperproliferative disorders, angiogenesis disorders, cell cycle regulation disorders, autophagy regulation disorders, inflammatory disorders, and/or infectious disorders and/or for enhancing cellular engraftment and/or wound repair, as a sole agent or in combination with other active ingredients.

SUMMARY OF THE INVENTION

In one embodiment, the present invention includes an McL-1 inhibitor selected from at least one of:

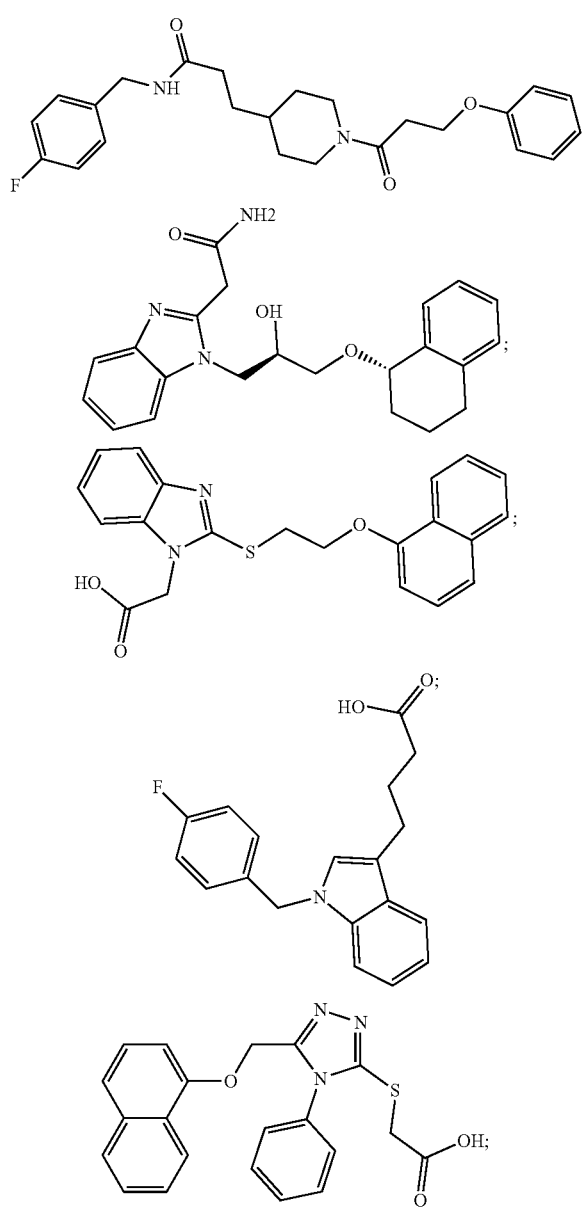

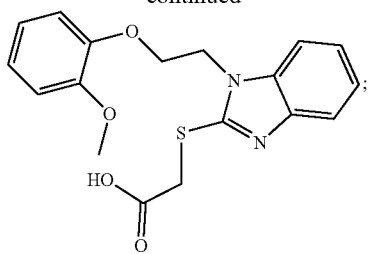
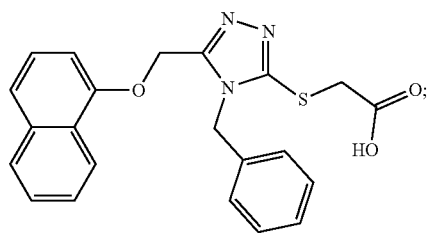
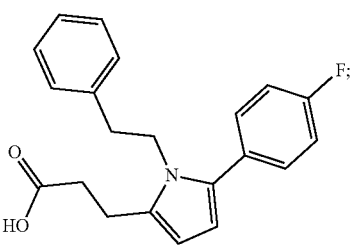
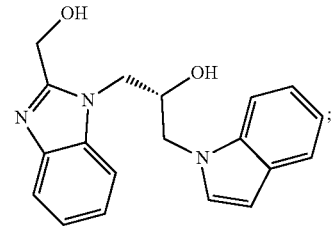
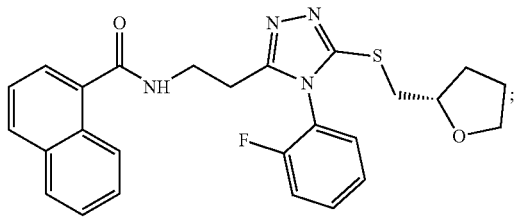
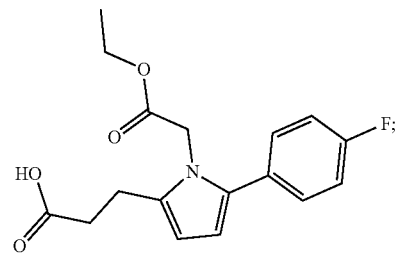
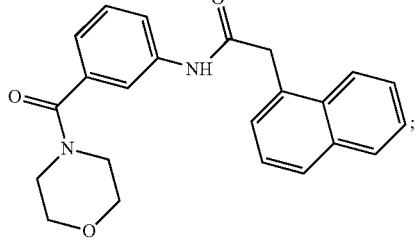
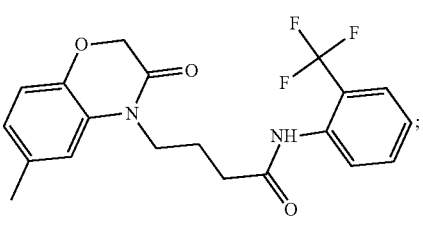
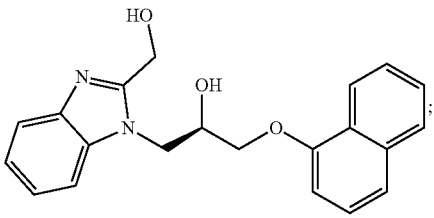
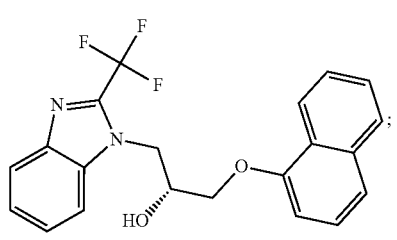
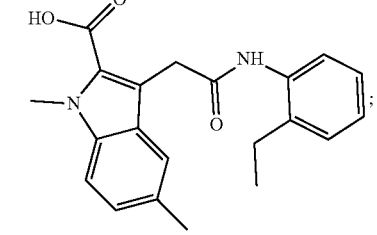
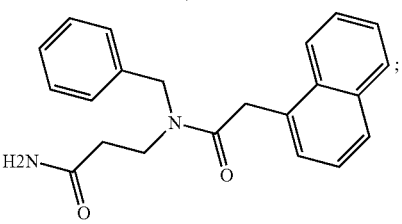
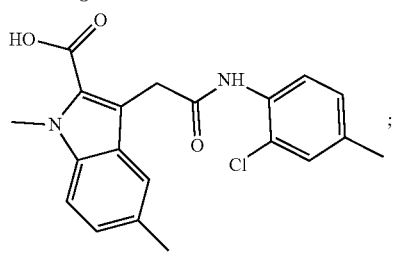

-continued
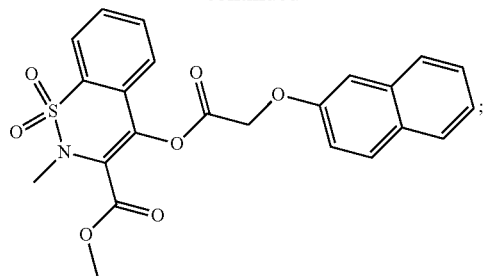
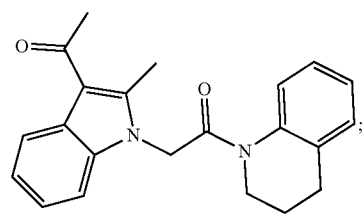
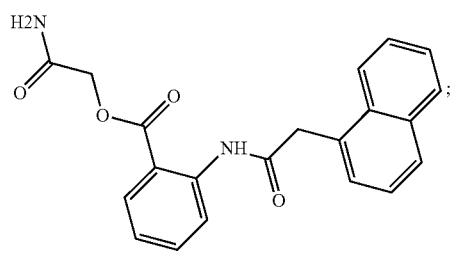
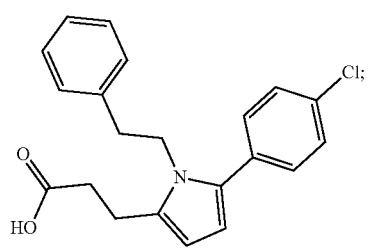
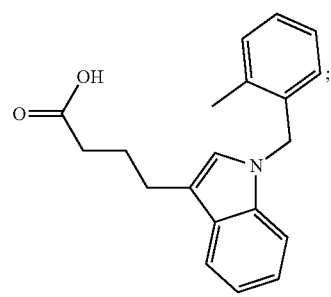
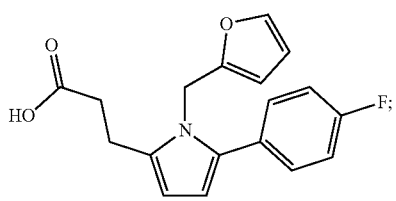
-continued
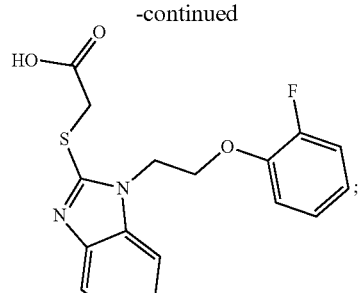
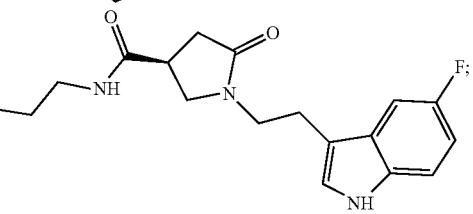
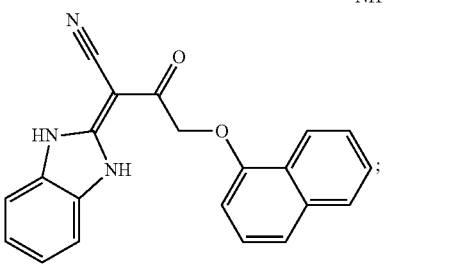
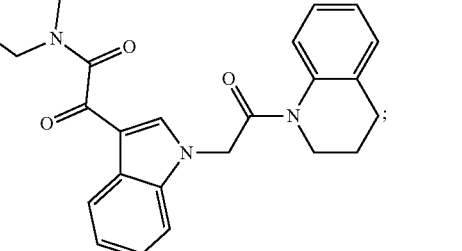
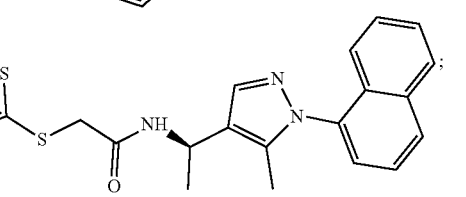
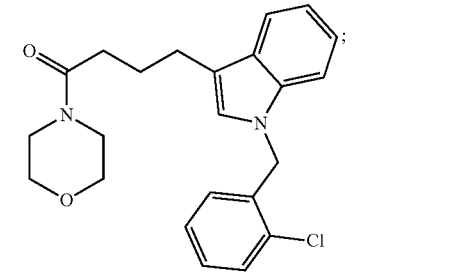

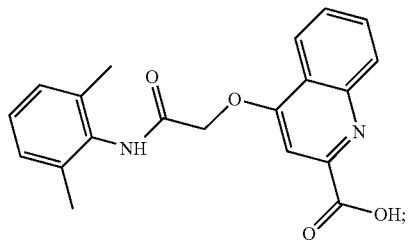
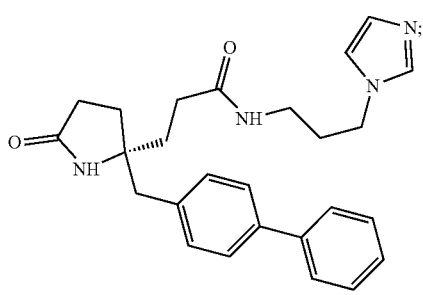
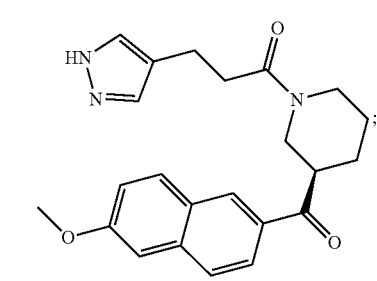
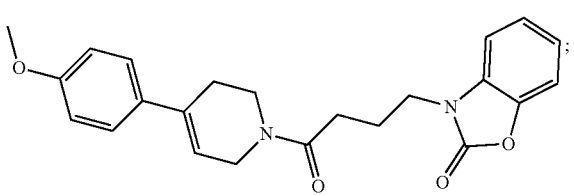
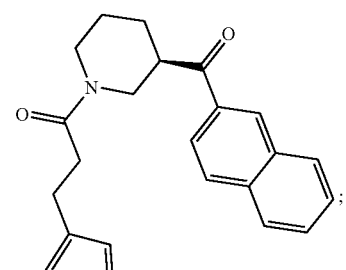
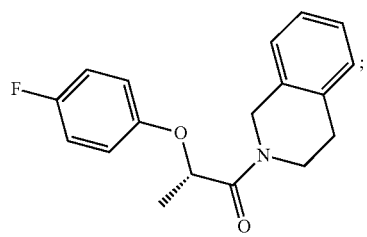
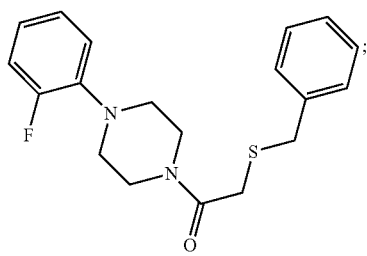
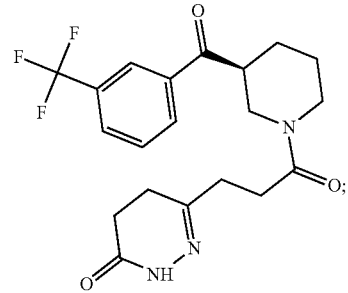
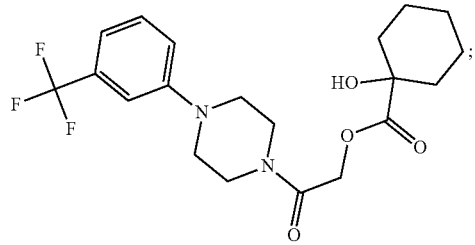
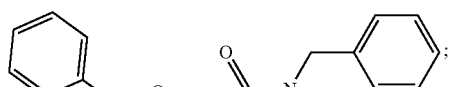
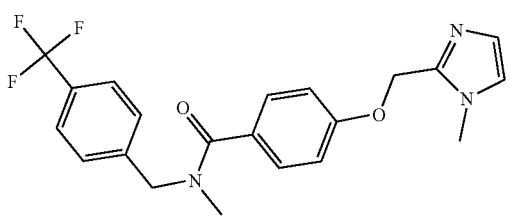
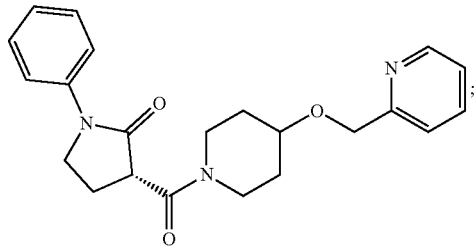
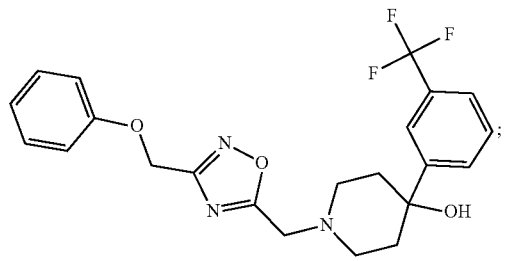

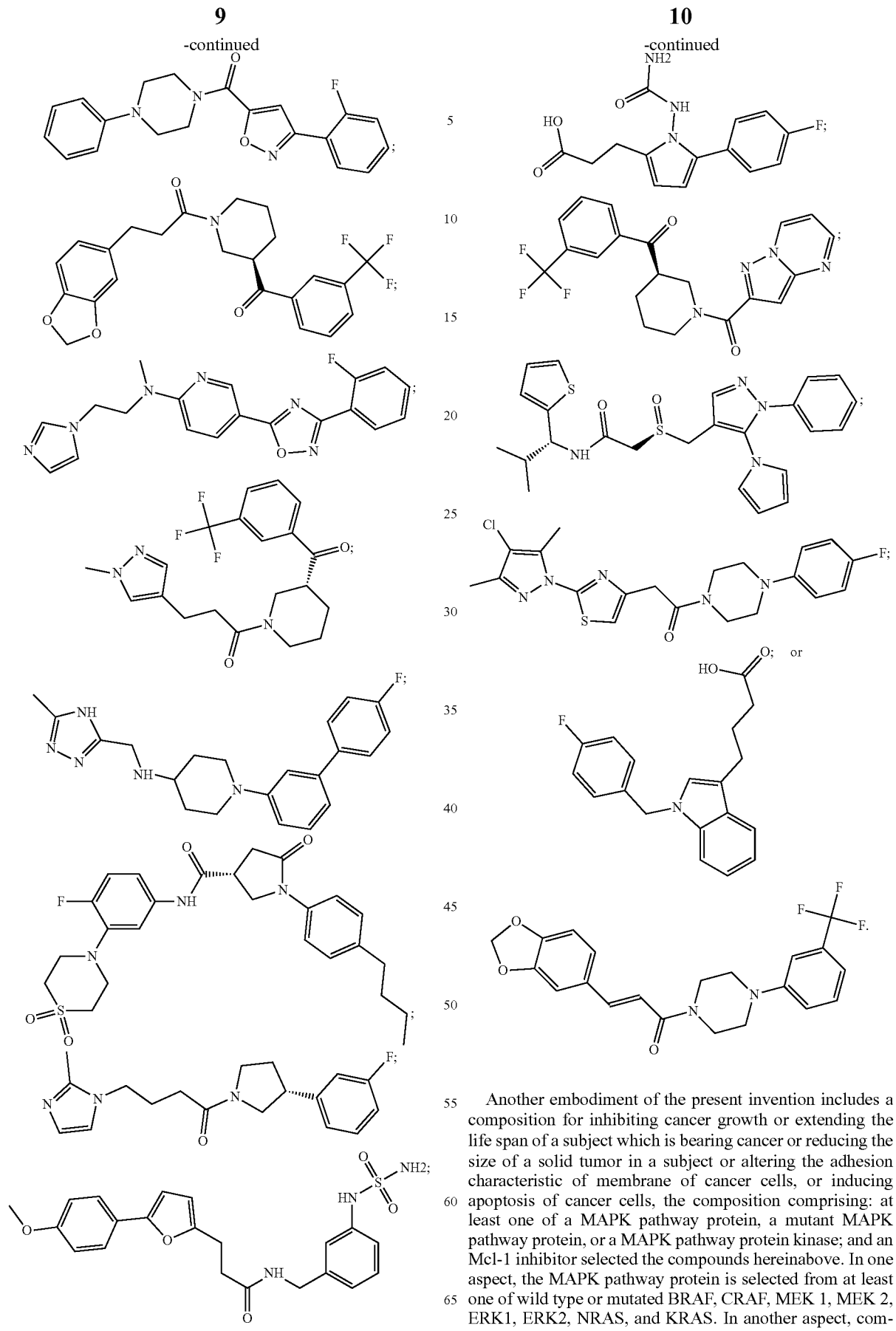

Another embodiment of the present invention includes a composition for inhibiting cancer growth or extending the life span of a subject which is bearing cancer or reducing the size of a solid tumor in a subject or altering the adhesion characteristic of membrane of cancer cells, or inducing apoptosis of cancer cells, the composition comprising: at least one of a MAPK pathway protein, a mutant MAPK pathway protein, or a MAPK pathway protein kinase; and an Mcl-1 inhibitor selected the compounds hereinabove. In one aspect, the MAPK pathway protein is selected from at least one of wild type or mutated BRAF, CRAF, MEK 1, MEK 2, ERK1, ERK2, NRAS, and KRAS. In another aspect, composition further comprises one or more Mcl-1 inhibitors selected from at least one of an antibody that blocks Mcl-1 activity, omacetaxine mepesuccinate, 2-(R)-(1-Ethyl-2-hydroxyethylamino)-6-benzylamino-9-isopropylpurine (Seliciclib), a small interfering RNA (siRNA) or a small hairpin RNA (shRNA) that inhibits expression of Mcl-1, antagonists of Mcl-1 isotype 1, agonists of Mcl-1 isotype 2, benzylisothiocyanate, phenethylisothiocyanate, diindolyl methane, curcumin, piperlongumine, Marinopyrrole A, Cucurbitacin B, Capsaicin, Penfluridol, Perphenazine, Bcl-2 inhibitors, Bcl-2 siRNA/shRNA, Bcl-XL inhibitors, Bcl-XL siRNA/shRNA and any other Bcl-2 family inhibitors, a small interfering RNA (siRNA) that inhibits expression of Mcl-1, or a salt thereof. In another aspect, the MAPK pathway protein or kinase inhibitor is selected from at least one of GDC-0879, PLX-4720, Sorafenib Tosylate, Dabrafenib, Trametinib, LGX818, Vemurafenib, or a salt thereof. In another aspect, the cells of the tumors or tumor metastases are relatively insensitive or refractory to treatment with the inhibitor of the MAPK pathway protein, the mutant MAPK pathway protein, or the MAPK pathway protein kinase as a single agent. In another aspect, the MAPK pathway protein is a wild type or a mutated BRAF and the inhibitor of the BRAF is a small interfering RNA (siRNA) that inhibits expression of BRAF or reduces the overall BRAF activity in a cell. In another aspect, the tumor is insensitive to the inhibitor of the MAPK pathway protein, the mutant MAPK pathway protein, or the MAPK pathway protein kinase administered alone. In another aspect, the tumor that overexpresses Mcl-1 is a primary tumor, or a tumor metastasis. In another aspect, the tumor is a colorectal cancer, thyroid cancer, melanoma, lung cancer and any other cancer treated with MAPK protein or kinase inhibitor.

Yet another embodiment of the present invention includes a method of treatment of a tumor which comprises administering to a subject in need of treatment an effective amount of an inhibitor of a MAPK pathway protein or kinase inhibitor sufficient to reduce the growth of or reduce the tumor, in combination with an Mcl-1 inhibitor, wherein the tumor at least one of overexpresses a MAPK pathway protein or kinase or overexpresses a mutant MAPK pathway protein, and overexpresses Mcl-1, wherein the tumor is a melanoma, and wherein the McL-1 inhibitor is selected from at least one of the compounds found hereinabove.

Being highly specific, Mcl-1 inhibitors of the present invention can be used to treat any type of cancers expressing Mcl-1 irrespective of BRAF mutation and MAPK activation. Further, the Mcl-1 inhibitors taught herein can be used in combination with any other chemodrugs, treatment of which induces Mcl-1, irrespective of BRAF and MAPK pathway.

DESCRIPTION OF THE DRAWINGS

For a more complete understanding of the features and advantages of the present invention, reference is now made to the detailed description of the invention along with the accompanying figures and in which:

In FIG. 1A A375 cells, and in FIG. 1B SK-MEL-28 cells, were treated with various concentrations of vemurafenib for 72 hours. Following the treatment, the cells were stained with sulforhodamine B and the surviving cells were quantified spectrophotometrically. The study was performed at least three times independently, each time with eight replicates and the data is expressed as mean±S.D. In FIG. 1C A375 cells, and in FIG. 1D SK-MEL-28 cells, were treated with 0.1, 0.2 and 0.4 µM vemurafenib for 72 hours. Following the treatment, cell lysates were prepared and the protein was subjected to western blotting and analyzed for Mcl-1, cleaved caspase 3 and cleaved PARP. Each study was performed at least three times independently. In FIG. 1E A375 cells, and in FIG. 1F SK-MEL-28 cells, were treated with 0.4 µM vemurafenib for 72 hours. Following the treatment, live cells were separated from dead floating cells and the lysates were prepared. The protein was subjected to western blotting and analyzed for Mcl-1. Each study was performed three times independently. TW-37 enhanced the efficacy of vemurafenib in melanoma cells by inhibition of Mcl-1. In FIG. 1G A375 cells, and in FIG. 1H SK-MEL-28 cells, were treated with 500 nM TW-37 one hour prior to treatment with 0.4 µM vemurafenib. The cells were stained with sulforhodamine B and the cell survival was evaluated spectrophotometrically. The study was performed at least three times independently, each time with four replicates and the data is expressed as mean±S.D. *, p<0.05 when compared with control. #, p<0.05 when compared with vemurafenib treatment. In a similar study, in FIGS. 1I and 1J, lysates of A375 cells (FIG. 1I), and SK-MEL-28 cells (FIG. 1J), were subjected to western blotting and analyzed for Mcl-1, cleaved caspase 3 and cleaved PARP. Each study was performed at least three independent times. β actin was used as loading control in all the western blots.

FIG. 2A shows that A375, A-375-R, A375X/R, SK-MEL-28 and SK-MEL-28-R cells were treated with various concentrations of vemurafenib for 72 hours following which the cell survival was analyzed by sulforhodamine B assay. The study was performed at least three times independently, each time with eight replicates and the data is expressed as mean±S.D. In FIG. 2B, lysates of A375, A375-R, A375-X/R, SK-MEL-28 and SK-MEL-28-R were subjected to western blotting and analyzed for Mcl-1. Each study was performed three times independently. Mcl-1 inhibitor overcomes vemurafenib resistance in melanoma cells. In FIG. 2C, A375-R, A375-X/R and SK-MEL-28-R cells were treated with 500 nM TW-37 one hour prior to the treatment with 0.4 µM vemurafenib. The cell survival was evaluated by sulforhodamine B assay. The study was performed at least three times independently, each time with four replicates and the data is expressed as mean±S.D. *, p<0.05 when compared with control. #, p<0.05 when compared with vemurafenib treatment. In FIG. 2D, in a similar study, lysates of A375-R, A375-X/R, and SK-MEL-28-R cells were subjected to western blotting and analyzed for Mcl-1, p-ERK, cleaved caspase 3 and cleaved PARP. Each study was performed at least three independent times. β actin was used as a loading control in all the western blots.

FIG. 3A (A375 cells) and FIG. 3B SK-MEL-28 cells untransfected or transfected with Mcl-1 plasmid were treated with 0.2 µM and 0.4 µM vemurafenib for 72 hours. The cell survival was evaluated by sulforhodamine B assay. The study was performed at least three times independently, each time with four replicates and the data is expressed as mean±S.D. *, p<0.05 when compared with control. In similar studies, FIG. 3C A375 and FIG. 3D SK-MEL-28 cells untransfected or transfected with Mcl-1 plasmid were treated with 0.4 µM vemurafenib for 72 hours. Following the treatment, the lysates were subjected to western blotting and analyzed for Mcl-1, cleaved caspase 3 and cleaved PARP. β Actin was used as a loading control. Each study was performed at least three times independently. FIG. 3E A375 and A375-Mcl-1+/+ or FIG. 3F, SK-MEL-28 and SK-MEL-28-Mcl-1+/+ were treated with 0.2 μM and 0.4 μM vemurafenib for 72 hours. The cell survival was evaluated by sulforhodamine B assay. The study was performed at least three times independently, each time with four replicates and the data is expressed as mean±S.D. *, p<0.05 when compared with control.

FIG. 5A, A375-R cells were injected subcutaneously in female athymic nude mice. Once the tumor volume reach 150 mm3, the mice were randomly divided into 4 groups (n=7 in each group) and the treatment was started as described under 'Material and Method' section. Tumor volumes were measure thrice a week by vernier calipers and the values were plotted as Mean±S.E.M. FIG. 5B, at day 30, the mice were sacrifice, tumors were extracted and weighed. The values are plotted as mean±S.D. *, p<0.05 as compared to control. #, p<0.05 as compared to vemurafenib treated group. $, p<0.05 as compared to TW-37 treated group. FIG. 5C, Tumor lysates from 6 mice were subjected to western blotting and analyzed for Mcl-1, p-ERK, cleaved caspase 3 and cleaved PARP. β actin was used as a loading control. FIG. 5D, Formalin fixed paraffin embedded tumor sections were subjected to immunohistochemistry. Representative images of the tumor sections stained with Mcl-1, p-ERK and cleaved caspase 3.

FIG. 6A, A375-R cells were injected subcutaneously in female athymic nude mice. Once the tumor volume reach 150 mm3, the mice were randomly divided into 4 groups (n=6 in each group) and the treatment was started as described under 'Material and Method' section. Tumor volumes were measure thrice a week by vernier calipers and the values were plotted as Mean±S.E.M. FIG. 6B, at day 30, the mice were sacrifice, tumors were extracted and weighed. The values are plotted as mean±S.D. *, p<0.05 as compared to control. #, p<0.05 as compared to vemurafenib treated group. $, p<0.05 as compared to TW-37 treated group. FIG. 6C, tumor lysates from 6 mice were subjected to western blotting and analyzed for Mcl-1, p-ERK, cleaved caspase 3 and cleaved PARP. β actin was used as a loading control. FIG. 6D, Formalin fixed paraffin embedded tumor sections were subjected to immunohistochemistry. Representative images of the tumor sections stained with Mcl-1, p-ERK and cleaved caspase 3.

FIGS. 7A to 7D, shows the Dabrafenib-Trametinib combination induces Mcl-1 expression in melanoma cells. A375, SK-MEL-28, SK-MEL-5 and WM-239 were treated (FIG. 7A) dabrafenib and trametinib and (FIG. 7B) vemurafenib and trametinib for 72 hours. Following the treatment, Mcl-1 expression was analyzed by western blotting. FIG. 7C, shows the cytotoxicity of dabrafenib at 72 hours in wildtype and resistant A375, SK-MEL-28 and WM-239 was evaluated by SRB assay. FIG. 7D, shows the expression of Mcl-1 in A375, SK-MEL-28 and WM-239 wild type cells dabrafenib resistant cells was evaluated by western blotting. β actin was used as a loading control in all the western blots. Each study was performed at least three times independently.

FIG. 8A (A375) and FIG. 8B (SK-MEL-28) untransfected or transfected with Mcl-1 plasmid were treated with 10 nM dabrafenib or 2 nM trametinib for 72 hours. FIG. 8C A375 and FIG. 8D SK-MEL 28 cells untransfected or transfected with Mcl-1 plasmid were treated with 400 nM vemurafenib or 2 nM trametinib for 72 hours. The cell survival was evaluated by sulforhodamine B assay. The study was performed at least three times independently, each time with four replicates and the data is expressed as mean±S.D. *, p<0.05 when compared with control. #, p<0.05 when compared with the respective untransfected controls. Each study was performed at least three times independently.

FIGS. 9A to 9D show that inhibiting Mcl-1 suppresses the growth of melanoma tumors resistance to vemurafenib. FIG. 9A A375-R cells were injected subcutaneously in female athymic nude mice. Once the tumor volume reach 150 mm3, the mice were randomly divided into 4 groups (n=7 in each group) and the treatment was started as described under 'Material and Method' section. PL was administered at a dose of 5 mg/kg by oral gavage daily. Tumor volumes were measure thrice a week by vernier calipers and the values were plotted as Mean±S.E.M. FIG. 9B at day 30, the mice were sacrifice, tumors were extracted and weighed. The values are plotted as mean±S.D. *, p<0.05 as compared to control. #, p<0.05 as compared to vemurafenib treated group. $, p<0.05 as compared to PL treated group. PL inhibits Mcl-1 in melanoma cells. FIG. 9C SK-MEL-28 and FIG. 9D shows Sk-MEL-2 cells were treated with 5, 7.5 and 10 μM PL for 48 hours. Cells were lysed, subjected to western blotting and analyzed for Mcl-1 and Cl.PARP. Actin was used as a loading control.

DESCRIPTION OF THE INVENTION

Figure 1:
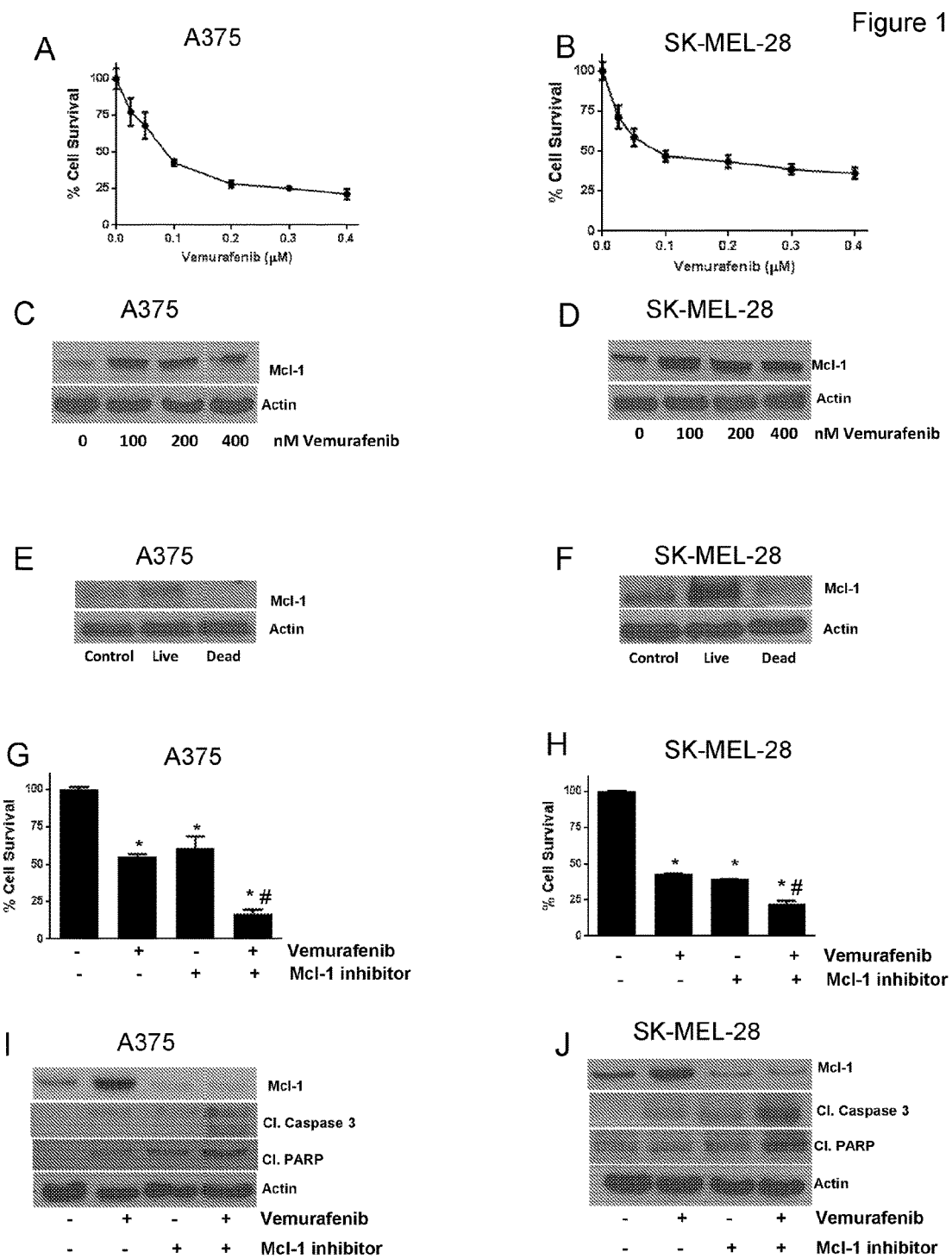
FIGS. 1A to 1J shows that Vemurafenib treatment induces Mcl-1 expression in melanoma cells.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Malignant melanoma harboring BRAF mutations frequently develop resistance to BRAF inhibitors, creating a major hurdle for treatment. The reason for resistance to BRAF inhibitors is not yet known, however, a possible mechanism of resistance is identified (but is not a limitation of the present invention) and a highly effective drug combination is demonstrated to overcome the resistance. Single treatment of A375 and SK-MEL-28 melanoma cells with vemurafenib or dabrafenib alone or in combination with trametinib resulted in overexpression of Mcl-1. Overexpression of Mcl-1 by transient transfection completely blocked BRAF and MEK1/2 inhibitor mediated inhibition of cell survival as well as cleavage of caspase 3 and PARP. Melanoma cells with stable overexpression of Mcl-1 were completely resistant to the treatment with BRAF inhibitors. Melanoma cells resistant to BRAF inhibitors showed significantly higher expression of Mcl-1 as compared to respective parent cell lines. Treatment of resistant cell lines with vemurafenib and Mcl-1 inhibitor resulted in remarkable growth inhibition. Silencing of Mcl-1 using siRNA completely sensitized resistant melanoma cells to cell growth suppression mediated by BRAF inhibitors. A375-R xenografts implanted in athymic nude mice did not respond to vemurafenib treatment but showed substantial tumor growth suppression when treated with a combination of vemurafenib with TW-37 or Mcl-1 siRNA. Immunohistochemistry and western blot analyses demonstrated enhanced expression of Mcl-1 in vemurafenib-resistant tumors whereas Mcl-1 expression in the tumors of mice treated with either of the combination was almost diminished. These results elucidate the mechanism of resistance to BRAF inhibitors and suggest that the combination of BRAF inhibitors with Mcl-1 targeted therapies may constitute a potential therapeutic advantage to melanoma patients with acquired resistance to BRAF inhibitors alone or in combination with MEK1/2 inhibitors.

Melanoma, a malignant transformation of melanocytes accounts for the highest number of skin cancer related deaths with a 5-year survival probability of less than 5%. Braf mutation is observed in almost 70% melanomas. Most common mutation in Braf is a single substitution of valine to glutamic acid at 600 codon (V600E), accounting for almost 90% Braf mutations in melanoma. Selective inhibitors targeting BrafV600E have shown significant clinical activity in the patients with late stage metastatic melanoma amongst which vemurafenib has been recently approved by US-FDA. In spite of promising initial response, there have been several recent reports of acquired resistance with 6-9 months of vemurafenib treatment in most of the patients. As a consequence, development of squamous cell carcinoma in about 20-30% of patients and tumor recurrence has been major limitations of vemurafenib therapy. The 'acquired resistance' occurs in the tumors that were earlier sensitive to vemurafenib treatment. The acquired resistance to vemurafenib has emerged as a major obstacle in the treatment of the patients with late stage malignant melanoma with BrafV600E mutation leading to poor prognosis. Hence, identification of the mechanism behind this acquired resistance and formulating a drug combination to overcome, is of prime importance.

Myeloid cell leukemia-1 (Mcl-1) is pro-survival member of Bcl-2, which is known to promote oncogenesis not through cell proliferation but by inhibition of apoptosis, hence leading to immortalization of malignant cells. Its expression is regulated by transcription factors like STATs, cAMP response elements and NFκB. Mcl-1 is frequently overexpressed in a variety of human cancers thereby providing protection to the tumor cells from apoptosis. Hence, Mcl-1 has been identified as an important target in majority of human cancers and several therapeutic strategies focusing on Mcl-1 inhibition are currently under development.

The present inventors establish herein that acquired resistance to vemurafenib in melanoma cells was due to overexpression of Mcl-1. Moreover, these results demonstrate that the combination of vemurafenib with Mcl-1 targeted therapies were successful in overcoming acquired resistance in melanoma in vitro and in vivo.

Chemicals. Vemurafenib, dabrafenib, trametinib and TW-37 were purchased from Selleck Chemicals (Houston, YX, USA). All the antibodies and Mcl-1 siRNA were procured from Cell Signaling Technology Inc. (Danvers, Mass., USA). Plasmid overexpressing Mcl-1 was acquired from Addgene (Cambridge, Mass., USA).

A375 was a kind gift from Dr. Tyler Wakenda (Rochester University, NY), which was originally purchased from ATCC (Manassas, Va., USA). SK-MEL-28 and WM-239 cells were purchased from ATCC. SK-MEL-5 was a kind gift from Dr. Randy Burd. The authenticity of these cell lines was confirmed by STR analysis at Texas Tech University Health Sciences Center core facility (Lubbock, Tex., USA). All the cell lines were cultured in Eagle's Minimum Essential Medium (EMEM) supplemented with 10% fetal bovine serum.

Generation of BRAF-inhibitor resistant cell lines. Vemurafenib resistant clones of A375 and SK-MEL-28 were generated by continuous exposure of cells to escalating concentrations of vemurafenib over a period of one year. The cells were treated with vemurafenib for 72 hours after which fresh media was added to the cells. The cells were allowed to recover for 24 hours after which they were again exposed to vemurafenib as shown in Table 1. In all, cells were exposed weekly to two treatments of vemurafenib for 72 hours each with a 24 hour recovery period between the treatments. The initial concentration of vemurafenib used was 0.2 µM which was eventually increased to as high as 10 µM. Similarly, dabrafenib resistant cells were cultured by incubating the cells with increasing concentrations of the drug for a period of 3 months as described above. The fold resistant was intermittently evaluated by cytotoxicity analysis. Vemurafenib resistant cell lines were referred to as SK-MEL-28-R or A375-R and dabrafenib resistant cell lines were referred to as A375-DR, SK-MEL-28-DR or WM-239-DR. Another type of resistant cell line generated was A375 xenograft-resistant (A375 X/R) cells. Here, A375 cells were injected subcutaneously in nude mice. When palpable tumors were formed, the mice were orally treated with 30 mg/kg vemurafenib twice a day. After a month, the tumors the resisted vemurafenib treatments were extracted and cultured in vitro. These cells were called as A375 X/R cells.

Cytotoxicity analysis. SK-MEL-28, A375, WM-239, SK-MEL-28-R, A375-R, A375-DR, SK-MEL-28-DR and WM-239-DR cells were treated with various concentrations of vemurafenib or dabrafenib and cytotoxicity analysis was performed by SRB assay as previously described by the present inventors (24, 25).

TW-37 treatment. SK-MEL-28, A375, SK-MEL-28-R, A375-R and A375-X/R were plated in a six-well plate at a density of 0.3×106 cells/well and left overnight to attach. Next day, cells were treated with 500 nM TW-37 for one hour followed by treatment with 0.4 µM vemurafenib for 72 hours. Cells were collected and processed for SRB assay or western blotting.

Mcl-1 overexpression. A375 or SK-MEL-28 cells were transiently or stably transfected with plasmid overexpressing Mcl-1 by nucleofection kit (Lonza, Basel, Switzerland) according to manufacturer's protocol and previously described by the inventors (26). Briefly, 2×106 cells were suspended in a reaction mixture from the kit specific to the cell line (Kit V for A375 and Kit R for SK-MEL-28 cells). The cells were transferred to the cuvettes and nucleofected using the nucleofector instrument (Amaxa, Cologne, Germany). To achieve stable overexpression, after transfection, cells were exposed to puromycin with an initial concentration of 1 μg/ml, which was gradually increased to 5 μg/ml. The resistant colonies were picked by colony picking cylinder and were cultured in presence of puromycin (5 μg/ml). Stable overexpression of Mcl-1 was intermittently tested by western blotting. A375 or SK-MEL-28 cells with stable overexpression of Mcl-1 were denoted as A375-Mcl-1+/+ or SK-MEL-28-Mcl-1+/+ respectively.

Mcl-1 silencing. Silencing of Mcl-1 was achieved according to the protocol described by the inventors (27). Briefly, 0.3×106 cells were plated in OPTI-MEM without antibiotics and transfected with either Mcl-1 siRNA or scrambled siRNA. Complexes were prepared by incubating 10 mM siRNA with 8 μl siPORT transfection reagent in 200 μl OPTI-MEM media without serum or antibiotic for 20 minutes. These complexes were then added to the cells. Six hours after transfection, complexes were replaced with fresh medium.

Tumor Therapy. All the studies involving animals were approved by the Institutional Animal Care and Use Committee. About 5-6 weeks old athymic nude mice (Charles River, Wilmington, Mass., USA) were allowed to acclimatize for one week prior to the beginning of the studies. Mice were injected subcutaneously with 3.5×106 A375-R cells. When the tumor volume reached to 150 mm3, mice were randomly segregated into several groups with 6-7 mice in each group. Vemurafenib, formulated as MBP was suspended at a desired concentration in a vehicle containing 2% Klucel LF and adjusted to pH 4 with HCl, was given at a dose of 25 mg/kg twice a day through oral gavage. TW-37 in PBS/ethanol/Tween 80 was administered intraperitonially at a dose of 30 mg/kg thrice a week. Mcl-1 or scrambled siRNA was administered twice a week directly into the tumors (intra-tumoral injection) as described by the inventors previously (27). Tumor measurements were taken thrice a week by vernier calipers and the volume was calculated by the formula V=length*(breadth)2/2 as previously described (28-30). At the end of the study, animals were sacrificed and tumors were excised and fixed in formalin for immunohistochemistry or flash frozen in liquid nitrogen for western blotting analysis as described previously by the inventors (31).

Immunohistochemistry. Expression of Mcl-1, Cleaved Caspase 3 and p-ERK in tumor samples were analyzed by immunohistochemistry in paraffin sections five mice from each group. The sections were deparaffinized and rehydrated using decreasing concentrations of ethanol. Antigen retrieval process was carried out by boiling the sections in citrate buffer (pH 6) for 10 minutes. Endogenous peroxides were quenched by incubating the sections in 3% hydrogen peroxide solution. Sections were blocked using 6% goat serum for 30 minutes after which they were exposed to primary antibody overnight. Following the incubation, the expression was detected using Ultravision ONE detection reagent (Thermo Fisher, Houston, Tex.) according to the manufacturer's protocol. The sections were then counterstained with Mayer's hematoxylin and dehydrated using increasing concentrations of ethanol and xylene and observed under the microscope (Olympus).

Statistical analysis. All the statistical analysis was performed using Prism 6.0 (Graph Pad software Inc., San Diego, Calif., USA). In vitro data was plotted as mean±S.D. of at least three independent studies and in vivo data was plotted as mean±S.E.M. Data was analyzed by Student's t-test or one way ANOVA followed by Tukey's post-hoc analysis for multiple comparisons. Differences were considered statistically significant at P<0.05.

Vemurafenib treatment induces Mcl-1 expression in melanoma cells.

To choose the working concentrations, the inventors initially performed a cell viability assay to determine the concentration dependent effects of vemurafenib. For this, the inventors used A375 and SK-MEL-28 melanoma cells, both of which harbor BRAF mutation at V600E. The IC50 of vemurafenib in A375 and SK-MEL-28 cells at 72 hours were 0.1 μM and 0.075 μM respectively (FIGS. 1A-B). Hence, based on these results, A375 and SK-MEL-28 cells were treated with 0.1, 0.2 and 0.4 μM vemurafenib for 72 hours (FIGS. 1C-D). These results showed a significant upregulation of Mcl-1 upon vemurafenib treatment in both the cell lines (FIGS. 1C-D). Vemurafenib treatment increased the expression of Mcl-1 in A375 cells by about 4.7, 5.2 and 4.5 fold and in SK-MEL-28 cells by 10, 11 and 14 fold respectively (FIGS. 1C-D). Although the viability of A375 and SK-MEL-28 cells treated with 0.4 μM vemurafenib (4×IC50) was reduced by 60%, a remarkable increase in Mcl-1 expression was observed (FIGS. 1C-D). These observations indicated that the increase in Mcl-1 expression observed was perhaps coming from the remaining 40% of live cells that were resistant to vemurafenib. The inventors separated the live and the dead cells after treatment and compared the levels of Mcl-1 by western blotting. These results showed that there was a diminished expression of Mcl-1 in the dead floating cells (FIGS. 1E-F). In contrast, the cells that survived upon vemurafenib treatment had significant upregulation of Mcl-1 as compared to control cells indicating that expression of Mcl-1 perhaps protected the cells from the cytotoxic effects of vemurafenib (FIGS. 1E-F).

Mcl-1 inhibitor enhances the growth suppressive effects of vemurafenib.

Since, it was observed that the cells that survived after vemurafenib treatment had significant upregulation of Mcl-1, the inventors determined whether TW-37, a Mcl-1 inhibitor, enhances vemurafenib mediated growth suppression. Vemurafenib (0.4 μM) treatment reduced the cell viability of A375 and SK-MEL-28 by 52% and 55% respectively (FIGS. 1G-H). TW-37 alone decreased the viability of A375 and SK-MEL-28 cells by 60% and 58% respectively (FIGS. 1G-H). However, the combination of vemurafenib and TW-37 treatment reduced the cell survival by 85% and 84%, which was significantly higher than any of the single treatments (FIGS. 1G-H). These observations correlated with the inventors' western blot results. Vemurafenib failed to upregulate Mcl-1 when cotreated with TW-37 (FIGS. 1I-J). The combination treatment significantly induced the cleavage of caspase 3 and PARP, which was higher than any of the single agent treatment indicating apoptosis (FIGS. 1I-J).

Vemurafenib resistant melanoma cells exhibit Mcl-1 overexpression.

Next, the levels of Mcl-1 in the cells with vemurafenib resistance were determined. Hence, the inventors generated A375-R, A375-X/R and SK-MEL-28-R vemurafenib resistant cell lines. The resistance in these cell lines was developed by treating the cells with increasing concentrations of vemurafenib over a period of one year according to the data shown in Tables 1 and 2.

Table 1 shows that the Resistance to vemurafenib in A375 cells was developed by treating the cells with escalating concentrations of vemurafenib. Cells were exposed to two treatments of vemurafenib in a week for 72 hours each. Cytotoxicity of these cells was evaluated intermittently by sulforhodamine B assay. Table 2 shows that the resistance to vemurafenib in SK-MEL-28 cells was developed by treating the cells with escalating concentrations of vemurafenib. Cells were exposed to two treatments of vemurafenib in a week for 72 hours each. Cytotoxicity of these cells was evaluated intermittently by sulforhodamine B assay.

TABLE 1

Development of resistance to vemurafenib in A375 cells

| | Month | | | | | | | | | | | | |
|---|---|---|---|---|---|---|---|---|---|---|---|---|---|
| | 0 | 1 | 2 | 3 | 4 | 5 | 6 | 7 | 8 | 9 | 10 | 11 | 12 |
| Vemurafenib ($\mu$M) | 0 | 0.2 | 0.2 | 0.4 | 0.4 | 0.8 | 0.8 | 1 | 1 | 4 | 8 | 8 | 10 |
| IC50 ($\mu$M) (A375) | 0.1 | 0.215 | 0.285 | 0.41 | 0.45 | 0.485 | 0.56 | 0.85 | 0.97 | 1.25 | 1.84 | 2.6 | 3 |
| Fold Resistance | 1 | 2.15 | 2.85 | 4.1 | 4.5 | 4.85 | 5.6 | 8.5 | 9.7 | 12.5 | 18.4 | 26 | 30 |

TABLE 2

Development of resistance to vemurafenib in SK-MEL-28 cells

| | Months | | | | | | | | | | | | |
|---|---|---|---|---|---|---|---|---|---|---|---|---|---|
| | 0 | 1 | 2 | 3 | 4 | 5 | 6 | 7 | 8 | 9 | 10 | 11 | 12 |
| Vemurafenib ($\mu$M) | 0 | 0.2 | 0.2 | 0.4 | 0.4 | 0.8 | 0.8 | 1 | 1 | 4 | 8 | 8 | 10 |
| IC50 ($\mu$M) SK-MEL-28 | 0.075 | 0.158 | 0.162 | 0.264 | 0.315 | 0.61 | 0.673 | 0.735 | 0.754 | 0.824 | 1.236 | 1.864 | 3.3 |
| Fold Resistance | 1 | 2.1 | 2.24 | 3.52 | 4.2 | 8.13 | 8.97 | 9.8 | 10.05 | 10.99 | 16.48 | 24.85 | 44 |

Figure 2:
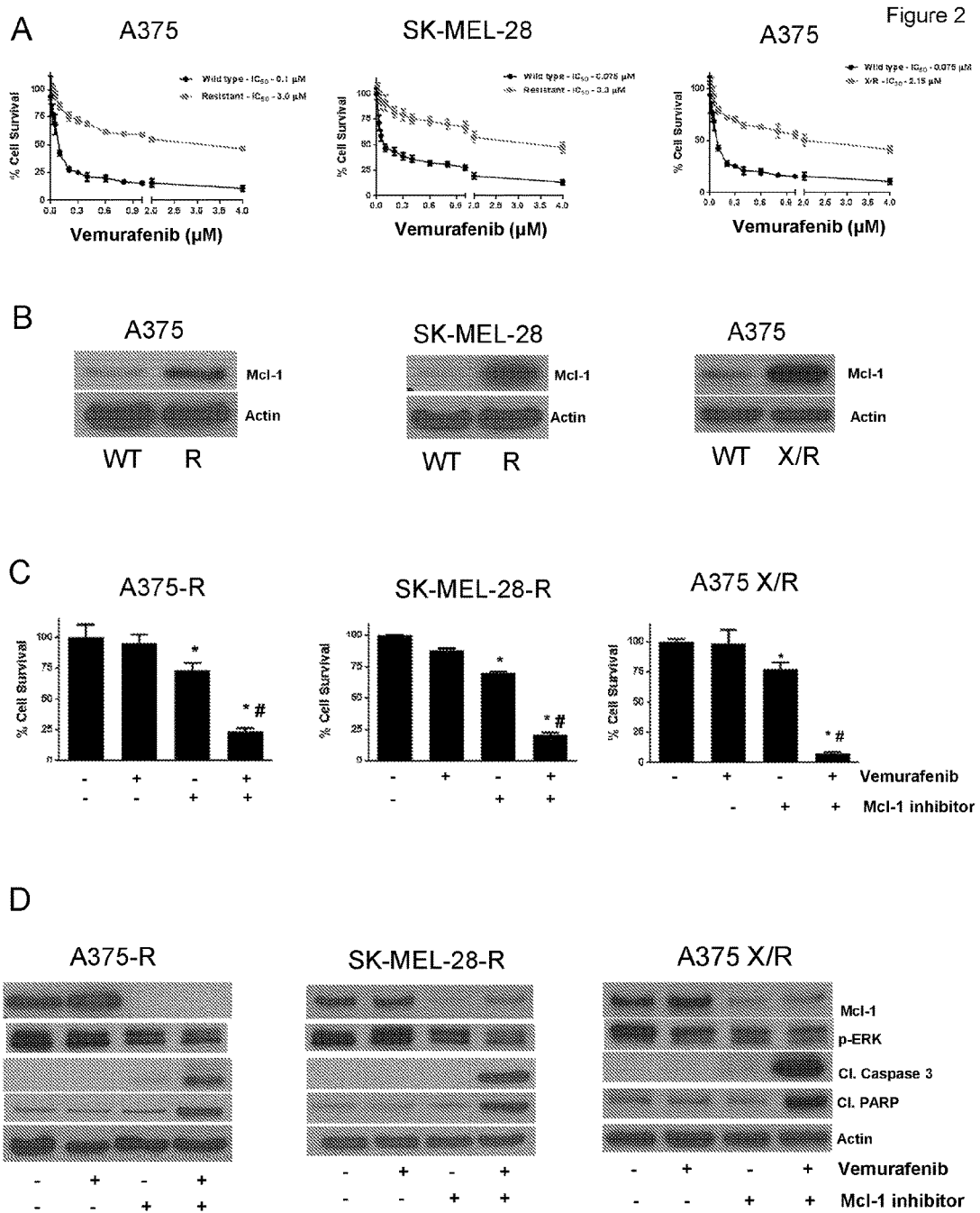
FIGS. 2A to 2D show Vemurafenib resistant melanoma cells exhibit Mcl-1 overexpression.

The IC50 of vemurafenib in A375R and A375 X/R was 3 $\mu$M and 2.15 $\mu$M, respectively, and that in SK-MEL-28R was 3.3 $\mu$M as compared to the IC50 of 0.1 $\mu$M and 0.075 $\mu$M in A375 and SK-MEL-28 parent cell lines (FIG. 2A). In all, the inventors achieved 30-40 fold resistance to vemurafenib in these cell lines. The resistant cells were absolutely not affected at the concentrations that suppressed more than 60% growth of the sensitive cell lines (FIGS. 1G-H and 2C). As expected, western blot results showed a massive increase in Mcl-1 expression in vemurafenib resistant cell lines (FIG. 2B). The fold increase in Mcl-1 expression in A375-R and A375-X/R was 6.2 and 4.83 respectively, and that in SK-MEL-28-R was 10.11 as compared to respective sensitive cells (FIG. 2B).

Mcl-1 inhibitor overcomes vemurafenib resistance in melanoma cells.

Vemurafenib, at a concentration of 0.4 $\mu$M, exhibited negligible effect on the survival of A375-R cells (FIG. 2C). The survival of A375-R cells when treated with TW-37 was decreased by 25% (FIG. 2C). However, when these resistant cells were treated with both TW-37 and vemurafenib, the survival of A375-R cells was decreased drastically by 80% (FIG. 2C). Similarly, in SK-MEL-28-R cells, vemurafenib showed minimal effect on cell survival but when combined with TW-37, the cell survival was drastically suppressed by about 80% (FIG. 2C). TW-37 treatment alone reduced the growth of SK-MEL-28-R cells by 25% only (FIG. 2C). The enhanced efficacy of vemurafenib when combined with TW-37 can be attributed to the inhibition of Mcl-1 making the cells sensitive to vemurafenib. Similar results were observed in A375-X/R cells (FIG. 2C). The western blot results showed substantial expression of Mcl-1 in control and interestingly vemurafenib treatment further increased the expression of Mcl-1 in all the resistant cell lines and almost no cleavage of caspase 3 in three cell lines (FIG. 2D). However, vemurafenib in combination with TW-37, which significantly inhibited Mcl-1, substantially increased the cleavage of caspase 3 and PARP indicating apoptosis (FIG. 2D). Furthermore, vemurafenib treatment did not have any effect on p-ERK but when combined with TW-37, there was a significant down-regulation of p-ERK (FIG. 2D). These results clearly indicated the role of Mcl-1 in inducing resistance to vemurafenib in malignant melanoma cells.

Mcl-1 overexpression reduces the sensitivity of melanoma cells to vemurafenib.

Figure 3:
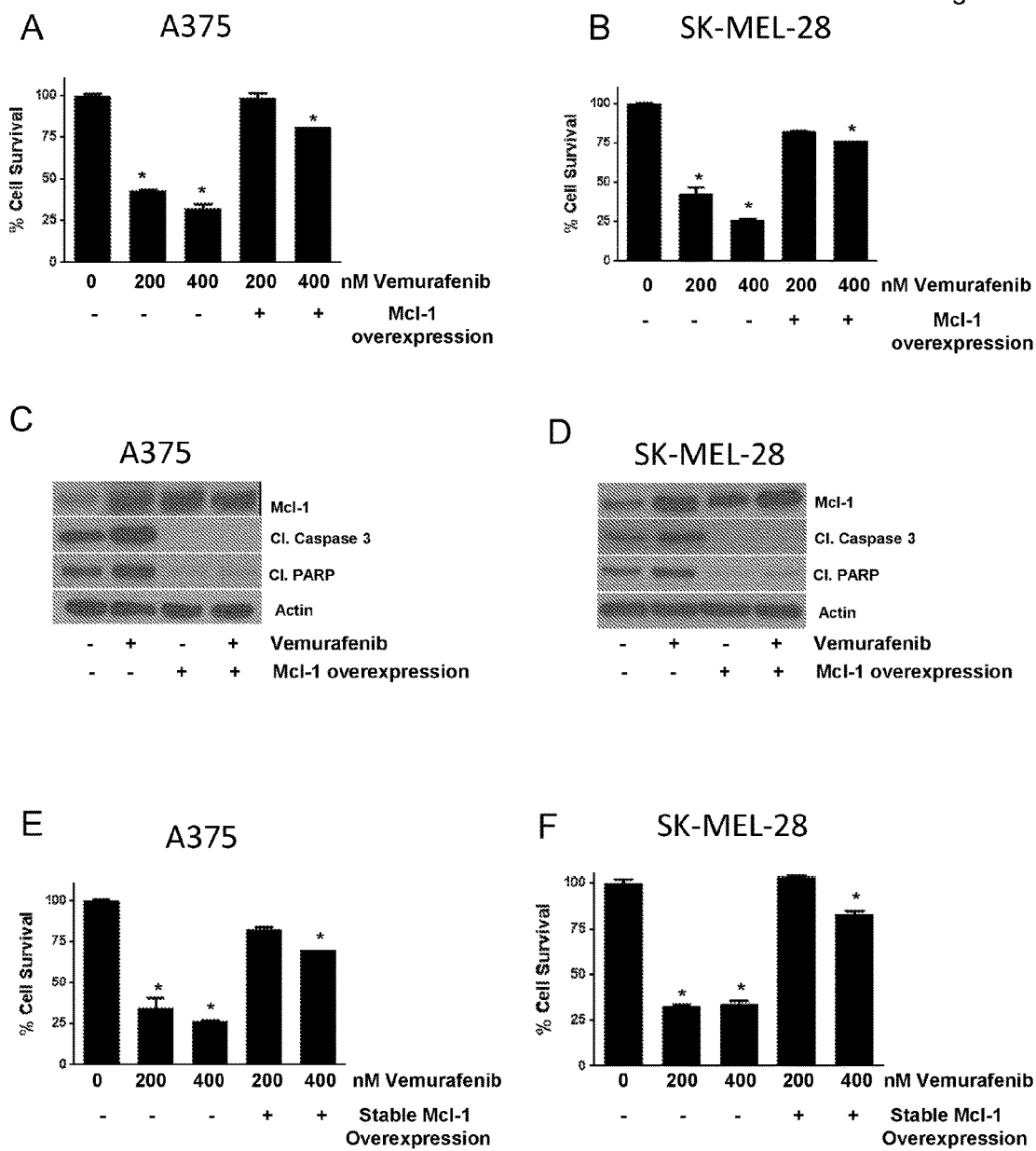
FIGS. 3A to 3F show that Mcl-1 overexpression reduces the sensitivity of melanoma cells to vemurafenib.

To further characterize the role of Mcl-1 in vemurafenib resistance, the inventors overexpressed Mcl-1 in A375 and SK-MEL-28 cells by transfecting the cells with Mcl-1 overexpressing plasmid. The survival of A375 cells was reduced by about 55% and 75% and SK-MEL-28 cells by 57% and 67% when treated with 0.2 $\mu$M and 0.4 $\mu$M vemurafenib respectively (FIGS. 3A-B). However, upon Mcl-1 overexpression, the effect of vemurafenib was significantly reduced in both the cell lines (FIGS. 3A-B). For example, the survival of Mcl-1 overexpressing A375 was reduced merely by 18% and 24% when treated with 0.2 $\mu$M and 0.4 $\mu$M of vemurafenib respectively (FIGS. 3A-B). Similarly, SK-MEL-28 cells overexpressing Mcl-1 were completely unaffected when treated with 0.2 $\mu$M vemurafenib whereas at 0.4 $\mu$M, the reduction in cell survival was only 18% (FIGS. 3A-B). These results were further supported by western blot results. Upon vemurafenib treatment, there was a significant cleavage of caspase 3 and PARP in both the cell lines, which was completely diminished upon Mcl-1 overexpression (FIGS. 3C-D).

To establish a connection between Mcl-1 and acquired vemurafenib resistance, the inventors generated A375-Mcl-1+/+ and SK-MEL-28-Mcl-1+/+ cell lines exhibiting stable overexpression of Mcl-1, and then evaluated the effect of vemurafenib in these cell lines. As expected, these cells behaved very similar to the resistant cells when treated with vemurafenib. The survival of A375-Mcl-1+/+ cells was reduced by only 20% and 25% when treated with 0.2 µM and 0.4 µM vemurafenib respectively (FIG. 3E). In SK-MEL-28-Mcl-1+/+ cells, no change was observed when treated with 0.2 µM vemurafenib but about 15% reduction in cell survival was observed when treated with 0.4 µM vemurafenib (FIG. 3F). In contrast, the respective wild type (parent) cells of both the cell lines were highly sensitive to vemurafenib treatment (FIGS. 3E-F). These results clearly establish the involvement of Mcl-1 in the induction of acquired resistance to vemurafenib in malignant melanoma cells.

Silencing Mcl-1 Reverses Vemurafenib Resistance.

Figure 4:
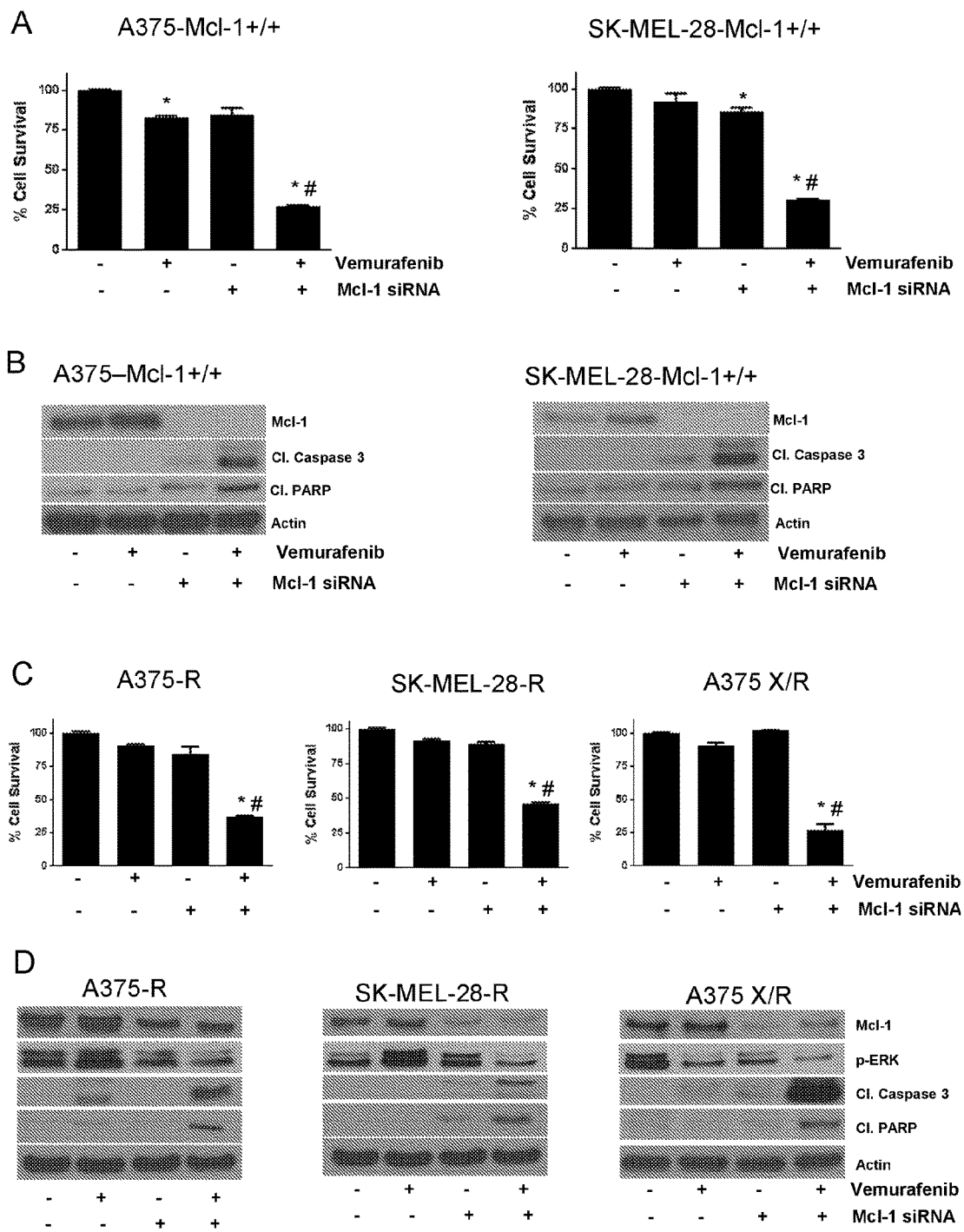
FIGS. 4A to 4D show the silencing Mcl-1 reverses vemurafenib resistance. Mcl-1 was silenced by siRNA in (FIG. 4A) A375-Mcl-1+/+, SK-MEL-28-Mcl-1+/+, (FIG. 4C) A375-R, A375-X/R and SK-MEL-28-R after which the cells were treated with 0.4 μM vemurafenib for 72 hours. The cell survival was evaluated by sulforhodamine B assay. The study was performed at least three times independently, each time with four replicates and the data is expressed as mean±S.D. *, p<0.05 when compared with control. #, p<0.05 when compared with vemurafenib treatment. In a similar study, after silencing of Mcl-1 by siRNA, (FIG. 4B) A375-Mcl-1+/+, SK-MEL-28-Mcl-1+/+ and (FIG. 4D) A375-R, A375-X/R and SK-MEL-28-R cell lysates were prepared and the protein was subject to western blotting and analyzed for Mcl-1, p-ERK, cleaved caspase 3 and cleaved PARP. Each study was performed at least three times independently.

To examine whether silencing Mcl-1 could overcome vemurafenib resistance in melanoma cells, Mcl-1 was silenced using siRNA. Silencing of Mcl-1 in all the cell lines was almost 100% (FIGS. 4B and 4D). The inventors first tested the effect of Mcl-1 silencing in A375-Mcl-1+/+ and SK-MEL-28-Mcl-1+/+ cells, since their response to vemurafenib was analogous to the resistant cell lines (A375-R and SK-MEL-28-R). As shown above, vemurafenib treatment had very minimal effect on A375-Mcl-1+/+ cells and was totally ineffective in SK-MEL-28-Mcl-1+/+ cells (FIG. 4A). However, upon silencing of Mcl-1 by siRNA, vemurafenib suppressed the survival of A375-Mcl-1+/+ cells by 73% and that of SK-MEL-28-Mcl-1+/+ cells by 70% (FIG. 4A). These observations were further supported with western blot results. With vemurafenib treatment, there was no change in the cleavage of caspase 3 and PARP as compared to control in both the cell lines (FIG. 4B). However, when Mcl-1 was silenced and the cells were treated with vemurafenib, apoptosis was induced as depicted by significant cleavage of caspase 3 and PARP (FIG. 4B). Next, the inventors determined the effect of vemurafenib in A375-R, A375-X/R and SK-MEL-28-R cells after silencing Mcl-1 as these cells expressed very high levels of Mcl-1. About 80-90% Mcl-1 silencing was achieved in all the resistant cell lines. Upon Mcl-1 silencing, there was a significant reduction in cell survival in all the resistant cell lines when treated with vemurafenib. The survival of A375-R, A375-X/R and SK-MEL-28-R cells when treated with vemurafenib was decreased by 65%, 75% and 55% respectively when Mcl-1 was silenced in these resistant cells (FIG. 4C). Moreover, the sensitivity of the Mcl-1 silenced resistant cells to vemurafenib was very similar to that of parent cells that the inventors observed earlier (FIGS. 1A-B). These results were further supported by western blot data (FIG. 4D). Vemurafenib treatment induced very minimal cleavage of caspase 3 and PARP in resistant cell lines (FIG. 4D). Nonetheless, treatment of cells with vemurafenib after silencing of Mcl-1 induced extensive cleavage of caspase 3 and PARP in the cells (FIG. 4D). Furthermore, vemurafenib treatment did not have any effect on p-ERK but when combined with Mcl-1 siRNA, there was a significant down-regulation of p-ERK (FIG. 4D). These results thoroughly established that inhibition of Mcl-1 completely overcomes the acquired vemurafenib in malignant melanoma cells.

Inhibiting Mcl-1 Suppresses the Growth of Melanoma Tumors Resistant to Vemurafenib.

Although it was very evident from the in vitro results that inhibition of Mcl-1 completely reversed the acquired resistance of melanoma cells to vemurafenib, it was important to translate these observations in vivo. As such, A375-R cells, which are completely resistant to vemurafenib, were injected subcutaneously in athymic nude mice. The tumors were allowed to grow till the tumor volume reached 150 mm3. The tumor bearing mice were then randomly divided into four groups so that each group had seven mice. In this study, a combination of vemurafenib with TW-37, which is a Mcl-1 inhibitor, was tested. The mice received 30 mg/kg TW-37 by intraperitoneal injection thrice a week and the tumors were also measured thrice a week. At day 30, the average tumor volume of the control group was 1613.5±231.9 mm3 while that of vemurafenib treated group was 1688±156.19 mm3 (FIG. 5A). The tumors did not respond to vemurafenib treatment at all. The tumor volume of the mice that were treated with TW-37 alone was 870±187.8 mm3 demonstrating a 48% and 46% reduction in tumor growths as compared to the tumor volumes of the mice from control as well as vemurafenib treated group, respectively (FIG. 5A). Most importantly, the mice that were treated with a combination of vemurafenib and TW-37 had tumor volumes that were drastically lower than all the three groups (FIG. 5A). The average tumor volumes of these mice at the end of the study were 215.3±51.6 mm3, showing an impressive reduction in tumor growth by more than 85% as compared to control or vemurafenib group (FIG. 5A). Surprisingly, the tumors did not grow much once the treatment started. At day 30, mice from all the groups were sacrificed and the tumors were removed and weighed. As shown in FIG. 5B, there was no difference in the tumor weight of control and vemurafenib treated mice. The weight of the tumor in TW-37 treated group was reduced by 47% as compared to control and 48% as compared to vemurafenib treated group (FIG. 5B). Notably, the tumor weight in the mice treated with TW-37 and vemurafenib was drastically reduced by more than 85%, consistent with tumor volume data. These results clearly indicate that Mcl-1 overexpression leads to acquired vemurafenib resistance and that inhibition of Mcl-1 sensitizes the vemurafenib resistant tumors to vemurafenib.

Mcl-1 Silencing Suppresses the Growth of Melanoma Tumors Resistant to Vemurafenib.

Since TW-37 is a chemical inhibitor, although fairly specific for Mcl-1, its off-target effects cannot be ignored. Hence, to further establish the role of Mcl-1 in vemurafenib resistance, the inventors determined the effect of vemurafenib in combination with Mcl-1siRNA in A375-R xenografts. These in vivo studies were performed as described above. The mice in treated group were injected with 20 µL Mcl-1 siRNA by intratumor injection twice a week. Scrambled siRNA was also injected to serve as control in another group. Tumor volumes were measured thrice a week. The average tumor volume of the mice that were treated with Mcl-1 siRNA alone at the end of the study was 875±134.3 mm3, which was significantly lower than that of control and vemurafenib treated mice (FIG. 6A). The average tumor volume of the mice treated with scrambled siRNA was 1553±650 mm3, showing no significant difference between the average volumes of the tumor of the mice treated with scrambled siRNA, vemurafenib or control mice (FIG. 6A). However, the average volume of the tumors in the mice that were treated with vemurafenib and Mcl-1 siRNA was 292±48.12 mm3, which once again showed a remarkable suppression of tumor growth by more than 80%, as compared to control or vemurafenib treated group (FIG. 6A). The weight of the tumor in Mcl-1 siRNA treated group was reduced by 40% as compared to control and 43% as compared to vemurafenib treated group (FIG. 6B). Notably, the tumor weight in the mice treated with Mcl-1 siRNA and vemurafenib was drastically reduced by more than 85%, consistent with tumor volume data (FIG. 6B). These results clearly establish the critical role of Mcl-1 in vemurafenib resistance and that combination of vemurafenib with Mcl-1 targeted therapy could overcome vemurafenib resistance in malignant melanoma sensitive to vemurafenib therapy.

Vemurafenib Resistant Tumors Exhibited Overexpression Mcl-1.

Figure 5:
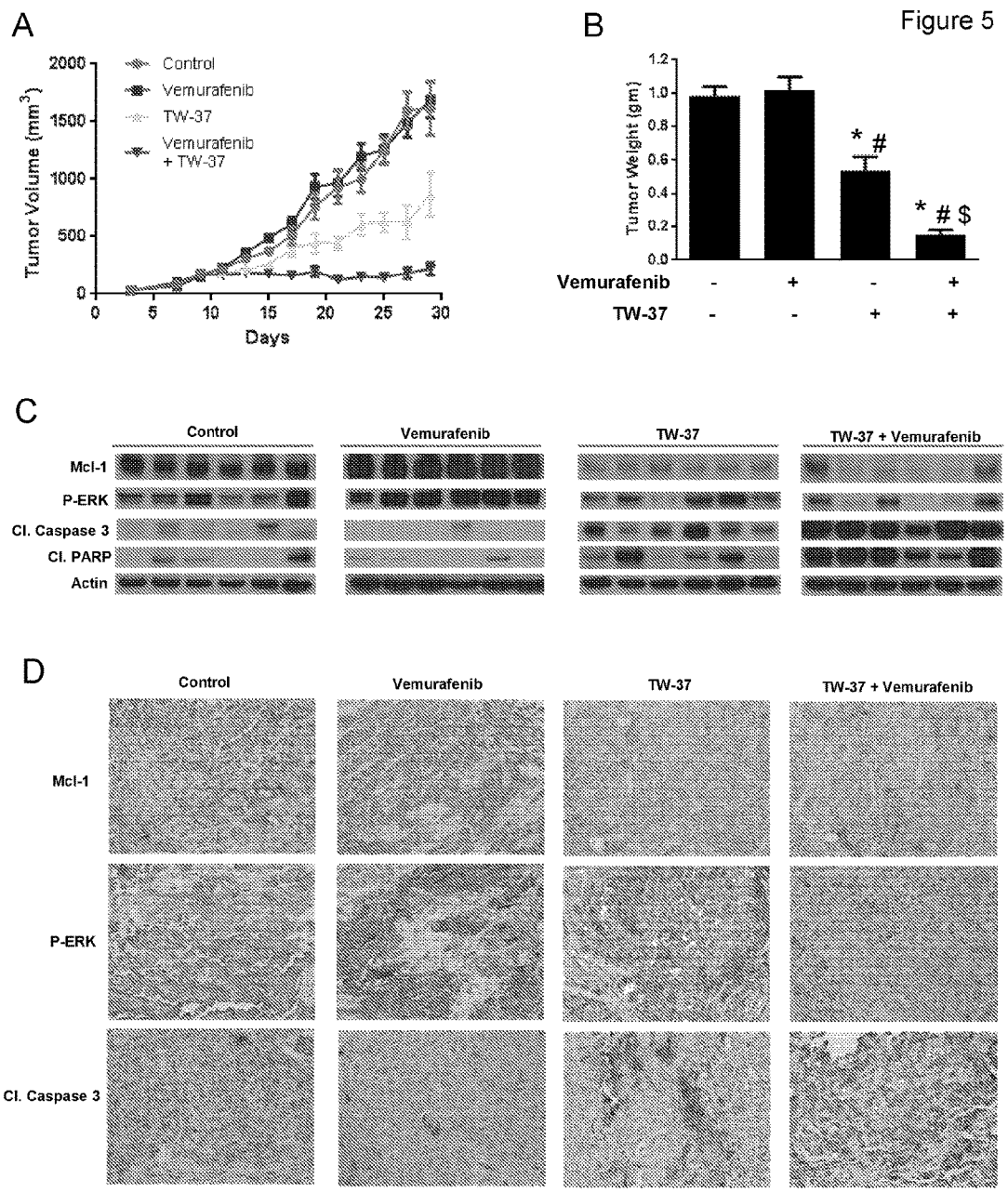
FIGS. 5A to 5D shows that inhibiting Mcl-1 suppresses the growth of melanoma tumors resistant to vemurafenib.
Figure 6:
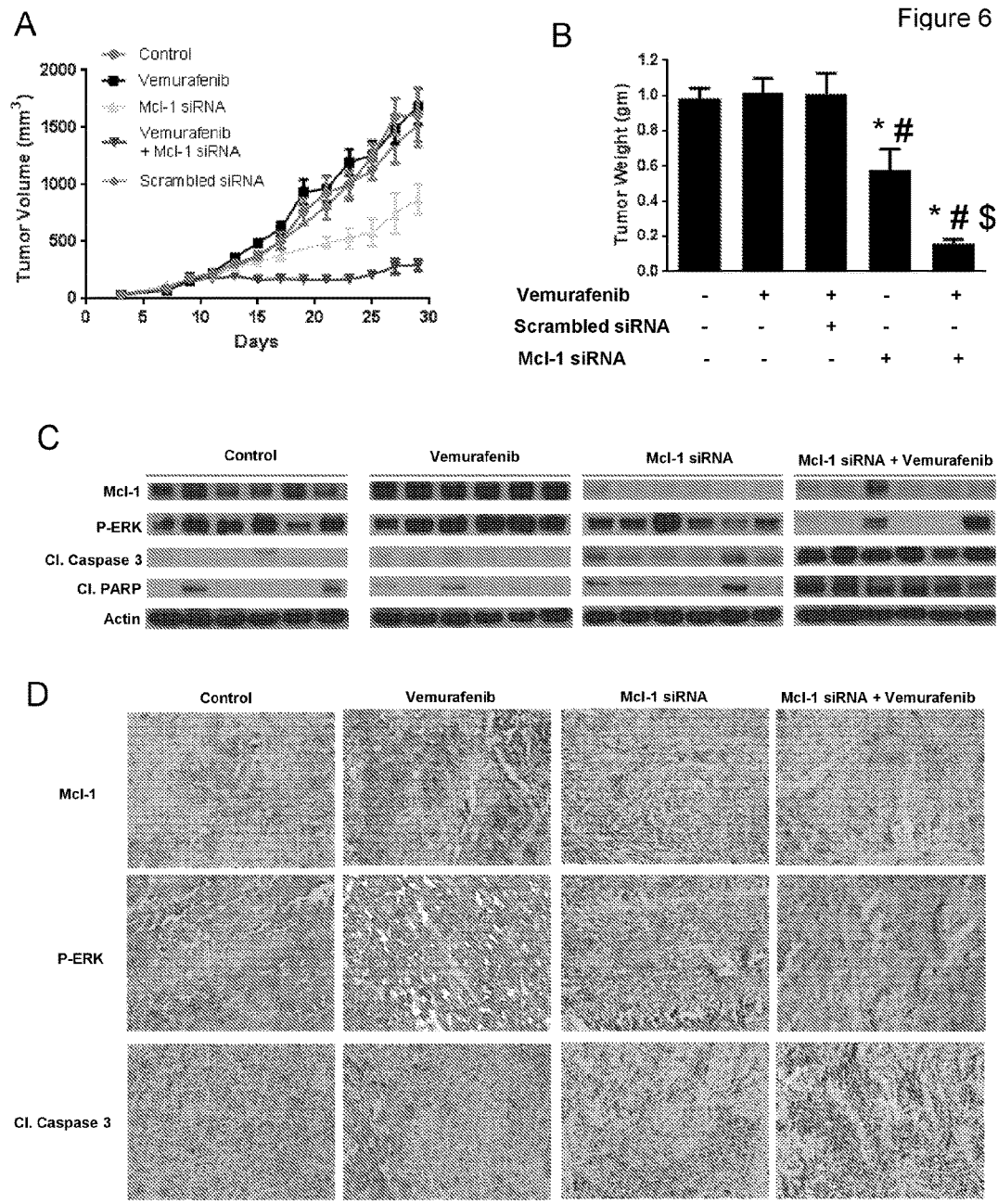
FIGS. 6A to 6D show silencing Mcl-1 suppresses the growth of melanoma tumors resistance to vemurafenib.

Upon termination of the in vivo studies, the tumors were examined by western blotting as well as immunohistochemistry. The control tumors showed marked expression of Mcl-1 (FIGS. 5 C-D and FIGS. 6 C-D). However, the tumors from vemurafenib treated group had significantly higher expression of Mcl-1 than the tumors from control group (FIGS. 5 C-D and FIGS. 6 C-D). The tumors that were treated with either Mcl-1 inhibitor (FIGS. 5C-D) or Mcl-1 siRNA (FIGS. 6C-D) had diminished expression of Mcl-1. Finally, the tumors that were treated with a combination of vemurafenib with either Mcl-1 inhibitor or Mcl-1 siRNA had significantly lower expression of Mcl-1 as compared to the tumors from control or vemurafenib treated group (FIGS. 5 C-D and FIGS. 6 C-D). The inventors also examined the expression of cleaved Caspase 3, cleaved PARP and p-ERK in these tumors. Tumors from control and vemurafenib group showed minimal cleavage of caspase 3 as well as PARP (FIGS. 5C-D and FIGS. 6 C-D). The tumors treated with Mcl-1 inhibitor or Mcl-1 siRNA showed modest cleavage of caspase 3 and PARP (FIGS. 5 C-D and FIGS. 6 C-D). However, the tumors that were treated the combination vemurafenib with Mcl-1 inhibitor or Mcl-1 siRNA showed massive cleavage of caspase3 and PARP. Expression of p-ERK was evaluated to check the inhibition of MAPK pathway. In control and vemurafenib treated group, where there was high expression of Mcl-1, the inventors also observed notable phosphorylation of ERK (FIGS. 5 C-D and FIGS. 6 C-D). Treatment with Mcl-1 inhibitor or Mcl-1 siRNA had minimal effect on p-ERK expression (FIGS. 5 C-D and FIGS. 6 C-D). However, upon combining vemurafenib with either Mcl-1 inhibitor or Mcl-1 siRNA, there was a substantial decrease in the phosphorylation of ERK, hence, indicating the inhibition of MAPK pathway (FIGS. 5 C-D and FIGS. 6 C-D).

Dabrafenib-Trametinib Combination Induces Mcl-1 Expression in Melanoma Cells.

A combination of BRAF inhibitor (dabrafenib) and MEK1/2 inhibitor (trametinib) for the treatment of late phase malignant melanoma has been approved by the FDA. Hence, the inventors determined whether the role of Mcl-1 in drug resistance is only specific to vemurafenib or applicable to other BRAF inhibitors as well. Hence, the inventors treated the cells with BRAF inhibitors (dabrafenib and vemurafenib) and MEK 1/2 inhibitor (trametinib) alone as well as in combination. The inventors observed that dabrafenib at a concentration of 10 nM significantly induced the expression of Mcl-1 in A375, SK-MEL-28, SK-MEL-5 and WM-239 cells (FIG. 7A). Moreover, trametinib treatment also induced Mcl-1 expression in all the melanoma cell lines (FIGS. 7A-B). Finally, treatment of melanoma cells with a combination of BRAF inhibitor and MEK1/2 inhibitor also caused remarkable induction of Mcl-1 (FIGS. 7A-B). These results indicated that BRAF inhibitors alone as well as in combination with MEK inhibitors induced Mcl-1 expression.

Dabrafenib-Trametinib Resistant Melanoma Cells Exhibit Overexpression of Mcl-1.

As the combination of dabrafenib and trametinib was recently approved, it would be too early to determine any incidences of resistant. However, the inventors sought to predict any occurrences of resistance based on the inventors' observations. Thus, dabrafenib and trametinib resistant A375, SK-MEL-28 and WM-239 cells were generated that are designated: A375-DR, SK-MEL-28-DR and WM-239-DR. The IC50 of dabrafenib in A375, SK-MEL-28 and WM-239 was 5 nM, 2 nM and 6 nM respectively, and that of A375-DR, SK-MEL-28-DR and WM-239-DR was greater than 100 nM (FIG. 7C). It was found that dabrafenib resistant melanoma cells also showed massive upregulation of Mcl-1 as compared to the respective wild type cells (FIG. 7D).

Mcl-1 Overexpressing Melanoma Cells are Resistant to Combined BRAF Inhibitor and MEK1/2 Inhibitor Treatment.

Figure 8:
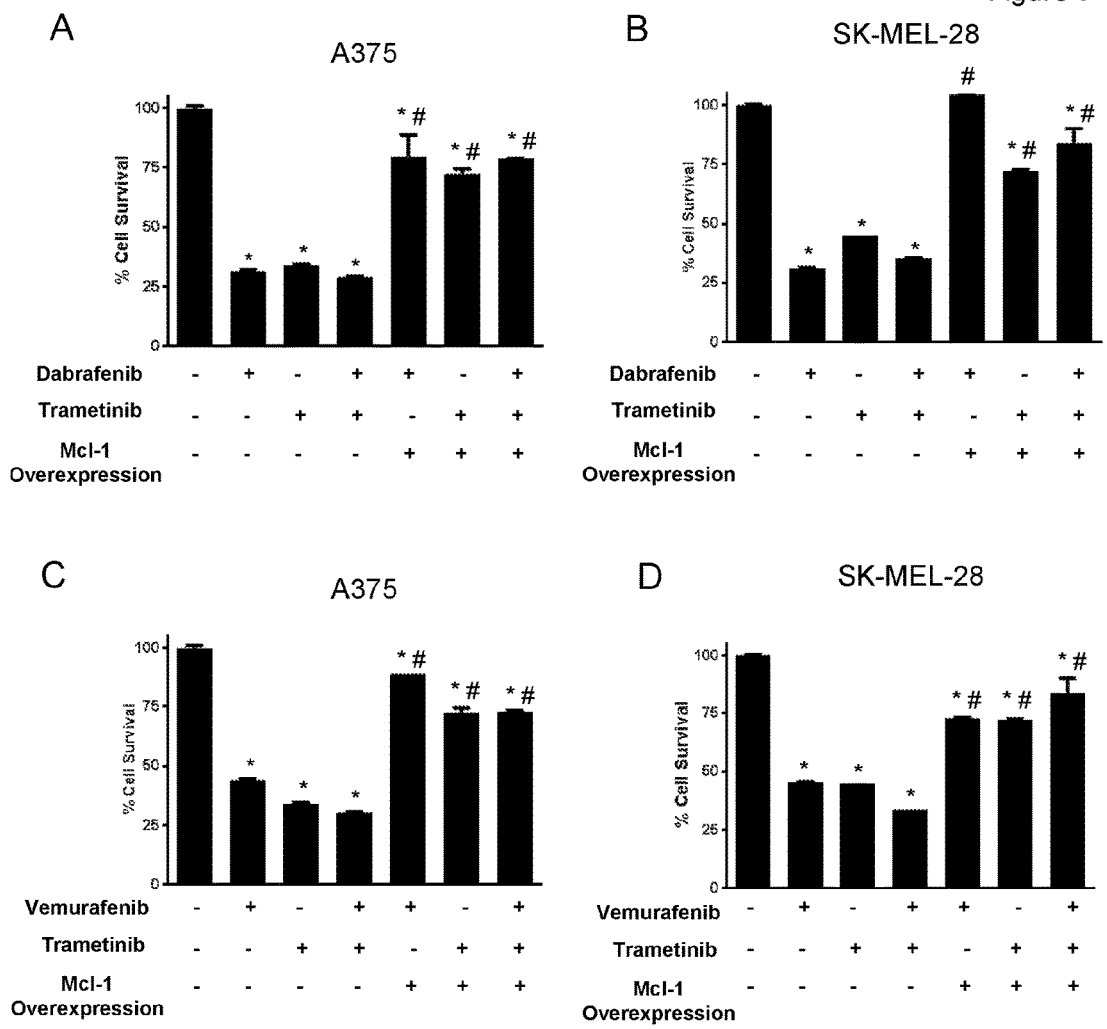
FIGS. 8A to 8D shows the Mcl-1 overexpressing melanoma cells are resistant to combined BRAF inhibitor and MEK1/2 inhibitor treatment.

To further characterize the role of Mcl-1 in resistance to the combination treatment of BRAF inhibitor with MEK1/2 inhibitor, the inventors determined the effect of Mcl-1 overexpression on efficacy of these therapeutic regimens. These results show that Mcl-1 overexpression not only reduced the efficacy of either BRAF inhibitor or MEK1/2 inhibitor alone but also their combination (FIGS. 8 A-D). For e.g. dabrafenib, trametinib or the combination reduced the survival of A375 and SK-MEL-28 cells by 60-70% (FIGS. 8A-B). However, upon Mcl-1 overexpression, the reduction in cell survival with any of the treatments was at the most 25% (FIGS. 8A-B). In SK-MEL-28, Mcl-1 overexpression completely blocked the effect of dabrafenib (FIG. 8B). Similar results were observed when Mcl-1 overexpressing melanoma cells were treated with a combination of vemurafenib and trametinib (FIGS. 8C-D).

FIGS. 9A to 9D show that inhibiting Mcl-1 suppresses the growth of melanoma tumors resistance to vemurafenib. FIG. 9A A375-R cells were injected subcutaneously in female athymic nude mice. Once the tumor volume reach 150 mm3, the mice were randomly divided into 4 groups (n=7 in each group) and the treatment was started as described under 'Material and Method' section. PL was administered at a dose of 5 mg/kg by oral gavage daily. Tumor volumes were measure thrice a week by vernier calipers and the values were plotted as Mean±S.E.M. FIG. 9B at day 30, the mice were sacrifice, tumors were extracted and weighed. The values are plotted as mean±S.D. *, p<0.05 as compared to control. #, p<0.05 as compared to vemurafenib treated group. $, p<0.05 as compared to PL treated group. PL inhibits Mcl-1 in melanoma cells. FIG. 9C SK-MEL-28 and FIG. 9D shows Sk-MEL-2 cells were treated with 5, 7.5 and 10 µM PL for 48 hours. Cells were lysed, subjected to western blotting and analyzed for Mcl-1 and Cl.PARP. Actin was used as a loading control.

Resistance to BRAF inhibitors has been the biggest hurdle in treatment of patients with malignant melanoma harboring BrafV600E mutation. These results demonstrated that overexpression of Mcl-1 in melanoma cells by treating the subject with not just a BRAF inhibitor treatment, but inhibitors of a MAPK pathway protein, a mutant MAPK pathway protein, or a MAPK pathway protein kinase can make the cells resistant to the therapy. The inventors observed massive overexpression of Mcl-1 in the cells with acquired BRAF inhibitor resistance as well as other proteins in the MAPK pathway. Melanoma cells whether transiently overexpressed with Mcl-1 or with stable overexpression of Mcl-1 demonstrated marked resistance to BRAF inhibitors alone or in combination with MEK1/2 inhibitor. On the other hand, inhibition of Mcl-1 in vemurafenib resistant cells by TW-37 or Mcl-1 siRNA rendered them highly sensitive to vemurafenib. The efficacy of the combination of vemurafenib and Mcl-1 targeted therapies was tested in vivo in the mice bearing tumors of vemurafenib resistant cells. Vemurafenib treatment had no effect on the tumor growth suppression but when combined with either TW-37 or Mcl-1 siRNA, drastic inhibition of the tumor growth was observed. To the best our knowledge, this is the first study that identifies BRAF inhibitor mediated overexpression of Mcl-1 as a mechanism of drug resistance to BRAF inhibitors in melanoma and combination of vemurafenib with Mcl-1 targeted therapies as a strategy to overcome the resistance.

Therapies involving several drug combinations have been tested to overcome vemurafenib resistance. Combination of vemurafenib with MEK inhibitors (32, 33) and PI3K/Akt/mTOR inhibitors (32, 34) has been studied in vitro. However, it is important to note that none of the studies so far established the mechanism of acquired resistance to vemurafenib, nor the treatment of the same in vivo. Moreover, the combinations reported in these studies have not been tested in vivo.

All the parent cells were highly sensitive to the treatment with BRAF inhibitor alone or in combination with MEK1/2 inhibitor. In spite of this, it was surprising to see a significant upregulation of Mcl-1 following a single treatment with BRAF inhibitors. The current results showed that vemurafenib treated cells that underwent apoptosis had diminished expression of Mcl-1 but on the other hand, the cells that survived after vemurafenib treated had very high levels of Mcl-1, which indicated that Mcl-1 overexpression could be the reason for the survival of the remaining cells. Subsequently, the cells resistant to BRAF inhibitors exhibited enhanced expression of Mcl-1. This convinced us that overexpression of Mcl-1 might be responsible for acquired resistance to BRAF inhibitors in melanoma cells.

A previous study has shown the induction of Mcl-1 by oncogenic BrafV600E in melanoma cells (35). Since BRAF inhibitors were developed to specifically target BrafV600E, theoretically, vemurafenib or dabrafenib should have suppressed the expression of Mcl-1, which was not observed by the present inventors. In fact, the opposite was observed. Not wanting to be bound by theory, it is possible (but not a limitation of the present invention) that the activation of some other pathways post treatment leading to upregulation of Mcl-1. Expression of Mcl-1 is promoted by various transcription factors like STATs, cAMP response elements and NFκB (14). Recent studies have correlated the activation of Src and STAT-3 with vemurafenib resistance (36, 37). Both these pathways can directly or indirectly regulate Mcl-1 expression. Moreover, activation of some other unknown pathway may also cause induction of Mcl-1 expression. Targeting upstream molecules may provide little benefit to overcome vemurafenib resistance as compared to targeting Mcl-1, as Mcl-1 is the ultimate downstream molecule and directly responsible for causing resistance to BRAF inhibitors. Moreover, since trametinib alone induced Mcl-1 expression, the induction of Mcl-1 may be responsible for the resistance to any inhibitors targeting the MAPK pathway, as shown herein.

Targeting upstream molecules for therapy often fails as the intermediary molecules often get mutated or influenced by cross talk with other pathways resulting in the ineffectiveness of therapy (38-40). The present inventors show herein using both in vitro and in vivo studies prove and establish Mcl-1 as the major culprit in inducing resistance to BRAF inhibitors in melanoma. Wild type A375 and SK-MEL-28 cells completely lost sensitivity to BRAF inhibitors alone or in combination with MEK1/2 inhibitors upon Mcl-1 overexpression and transformed them into resistant cells.

The role of Mcl-1 in resistance to BRAF inhibitors was confirmed when vemurafenib resistant A375-R or SK-MEL-28-R cells were treated with vemurafenib and TW-37 (Mcl-1 inhibitor) or Mcl-1 siRNA and showed tremendous inhibition of survival of both the cell lines. These cells were completely resistant to vemurafenib and the concentration of TW-37 or Mcl-1 siRNA that was used had marginal effect on cell survival.

TW-37 is a Mcl-1 inhibitor (41) with affinity for Bcl-2 and Bcl-XL and has shown to be effective in inhibiting the growth of various types of cancers but has not been tested in melanoma (42, 43). The combination of vemurafenib and TW-37 dramatically inhibited the growth of A375-R tumors. Surprisingly, the average volume of vemurafenib treated tumors was slightly more than that of control tumors, although not significant, showing that vemurafenib treatment was completely ineffective against vemurafenib resistant tumors. To rule out the off target effects of TW-37, the in vivo observations were further confirmed by using Mcl-1 siRNA along with vemurafenib. Mcl-1 siRNA in combination with vemurafenib remarkably halted the growth of vemurafenib resistant tumors, which otherwise did not respond to vemurafenib treatment alone.

Taken together, these results conclusively establish that overexpression of Mcl-1 is responsible for the resistance to BRAF inhibitors; the process mediated by BRAF inhibitors itself. Mcl-1 targeted therapies will have significant impact on the patients with melanoma tumors refractory to BRAF inhibitors. These results can eventually be extended to other cancers like colorectal and thyroid cancers having BRAF mutation. Our laboratory is working aggressively to extend these observations in other cancer models with BRAF mutations. Although, currently there is no FDA approved Mcl-1 inhibitor, the process to discover clinically useful Mcl-1 inhibitors has well begun (22, 23, 44, 45).

As discussed hereinabove, treatment options for late stage metastatic melanoma are limited. Studies have shown about 60% melanoma expressing mutant BRAF (V600E) oncoprotein. Studies have also shown high dependence of melanoma on BRAF (V600E). Therefore, FDA approved a BRAF (V600E) inhibitor to treatment of late stage metastatic melanoma bearing mutant BRAF. Although patients with malignant melanoma showed tumor regression and improved survival with vemurafenib treatment, most of the patients relapsed with lethal drug resistant disease, the mechanism of which is still unknown. As shown hereinabove, the up-regulation of Mcl-1, an important anti-apoptotic protein, upon vemurafenib treatment led to resistance. A combination of vemurafenib with an Mcl-1 inhibitor(s) helped overcome vemurafenib resistance. Due to malignant melanoma resistance when treated with a single agent BRAF inhibitor, a combination of BRAF inhibitor (Dabrafenib) and MEK 1/2 inhibitor Trametinib has been approved by the U.S. Food and Drug Administration (FDA). However, the present inventors determined that there was a significant upregulation of Mcl-1 when the cells were treated with Dabrafenib+Trametinib. Moreover, Mcl-1 expression was also induced when the cells were treated with either Dabrafenib or Trametinib alone. Moreover, melanoma cells overexpressing Mcl-1 did not respond to either single treatment with Dabrafenib or Trametinib or to the their combination. Hence, these results show that overexpression of Mcl-1 is not only a mechanism of resistance for vemurafenib but the entire class of BRAF inhibitors. Moreover, upregulation of Mcl-1 with Trametinib treatment may suggest that this mechanism can be extended to any inhibitors targeting the MAPK pathway. Hence, the present inventors sought to identify novel inhibitors of Mcl-1.

Scanning the pdb databank (www.wwpdb.org), two good quality crystal structures (3WIX.pdb and 4OQ6.pdb) were analyzed for MCL-1. As the bound small molecules to MCL-1 are different chemotypes, they led to different residues at the active site. Furthermore, from ChEMBL (European Bioinformatics Institute database), the inventors obtained 1514 known MCL-1 inhibitors. Unfortunately, none of these known MCL-1 inhibitors are very specific inhibitors. Thus, the inventors eliminated these earlier reported inhibitors from the screening library. Then, using a 3-tier docking algorithm (by gradually increasing the stringent characters), a 10 million drug-like compound library was screened against MCL-1. The 3-tiered protocol was necessary to increase the throughput of the docking studies and improve the quality of hits that are identified. As most compounds in the large compound database (ZINC database, zinc.docking.org) are unlikely to bind any one particular target, the first-tier screen rapidly eliminates molecules that fail to meet basic receptor-binding criteria like the shape and size. The second-tier screen further increases the stringency of the ligand-target binding criteria and identifies many compounds that may bind the target. Finally, the most computationally intensive third-tier screen performs robust modeling of the putative ligand-target binding interaction considering the electrostatic and hydrophobic interactions between the ligands and the target. This greatly increases the hit rate of the final hit set and results in a highly enriched set of compounds. This screening generated 709 hit compounds from 10 million compound database. In order to get consensus docked pose and scores, utilizing an orthogonal docking engine (secondary docking tool) to these 709 hits, the inventors obtained 78 compounds showing similar binding poses and scores in both the studies. Finally, a solubility test was conducted and 59 compounds passed the final solubility filtering. The following are the compounds identified as MCL-1 inhibitors.

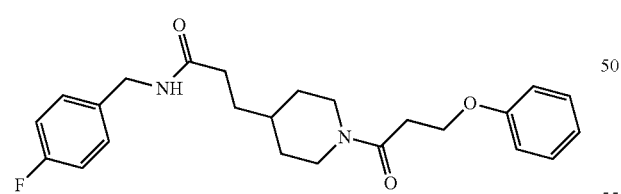

Title: ZINC12752049_000

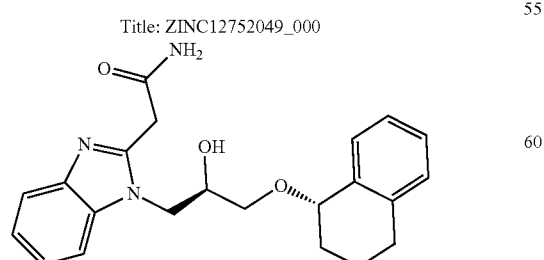

Title: ZINC43647199_000

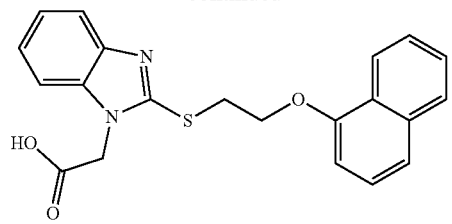

Title: ZINC03011959_000

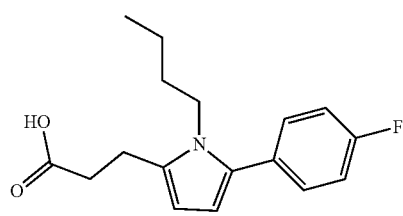

Title: ZINC02837602_000

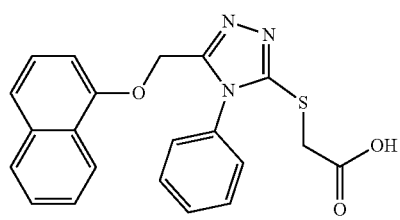

Title: ZINC04839173_000

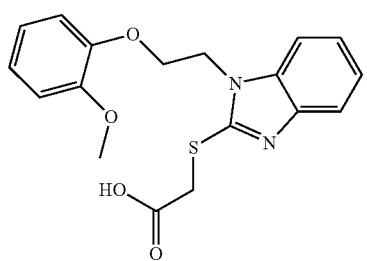

Title: ZINC04019643_000

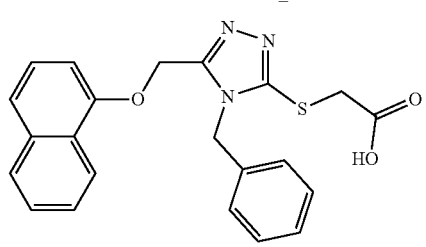

Title: ZINC04828323_000

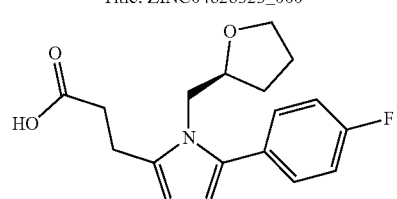

Title: ZINC02886288_000

-continued
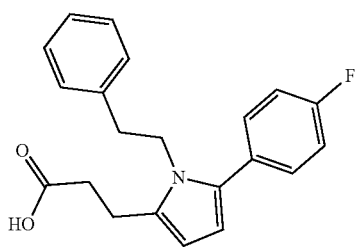
Title: ZINC00469923_000
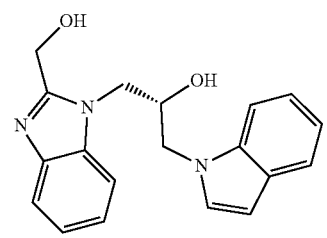
Title: ZINC01057726_000
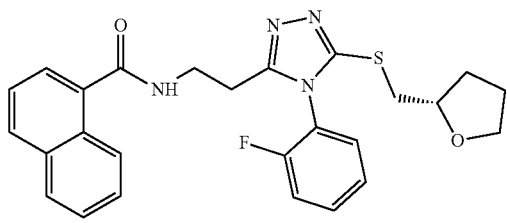
Title: ZINC11913505_000
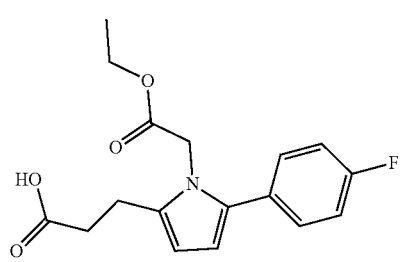
Title: ZINC00469762_000
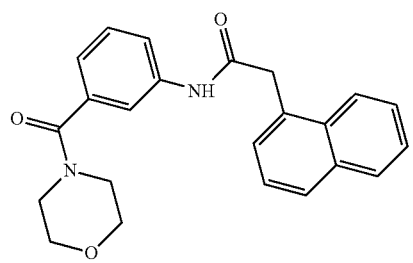
Title: ZINC00803411_000
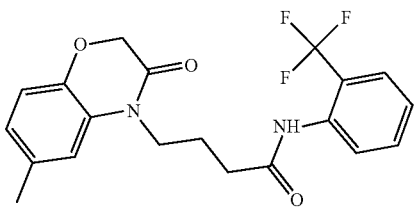
Title: ZINC20413268_000
-continued
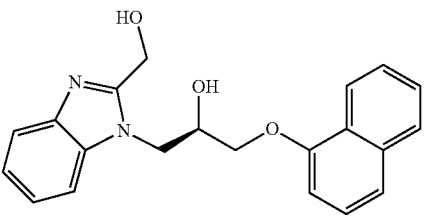
Title: ZINC21275464_000
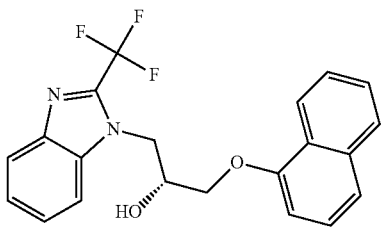
Title: ZINC01153246_000
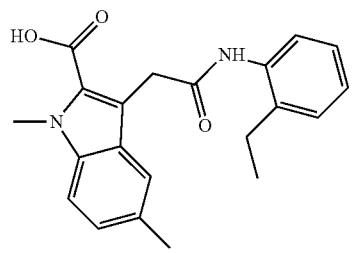
Title: ZINC04821822_000
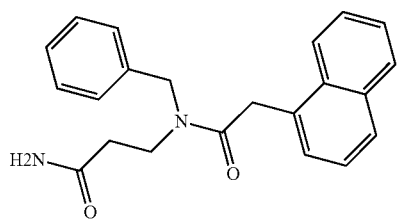
Title: ZINC14246273_000
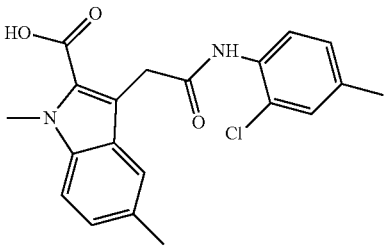
Title: ZINC04821809_000
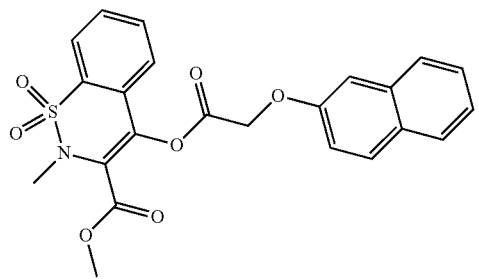
Title: ZINC20894095_000

-continued
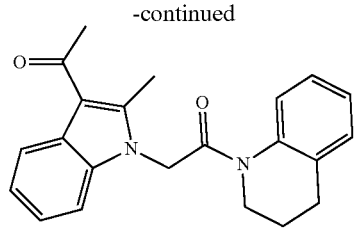
Title: ZINC02877769_000
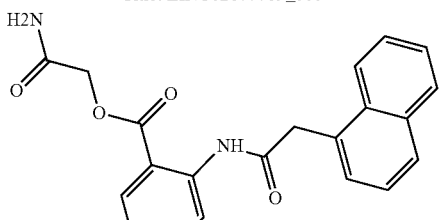
Title: ZINC05017731_000
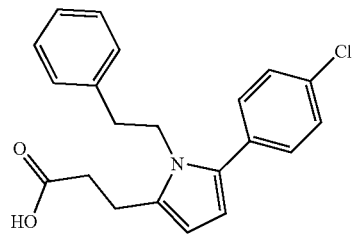
Title: ZINC01147821_000
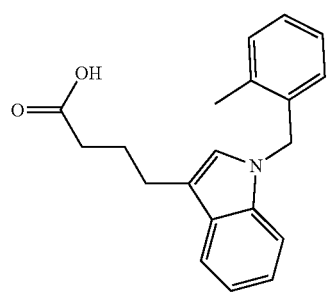
Title: ZINC06751205_000
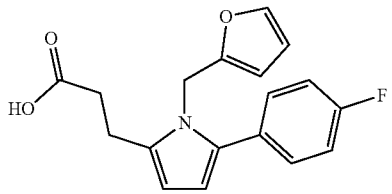
Title: ZINC00470123_000
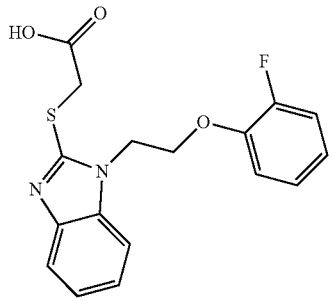
Title: ZINC04094992_000
-continued
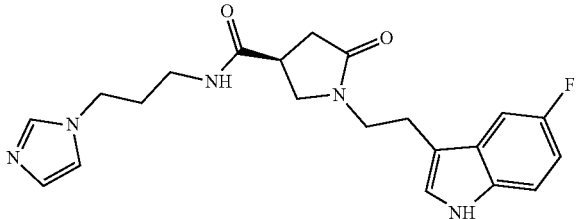
Title: ZINC13944868_000
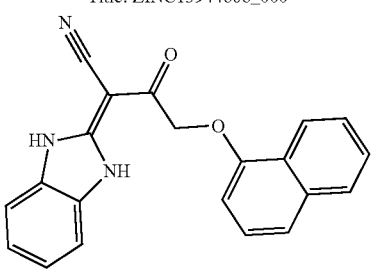
Title: ZINC05596036_000
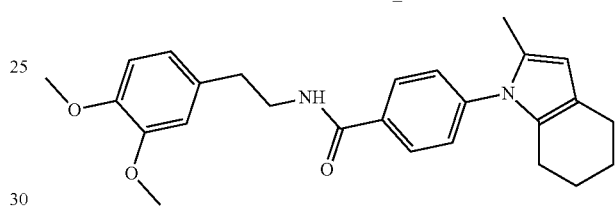
Title: ZINC06877858_000
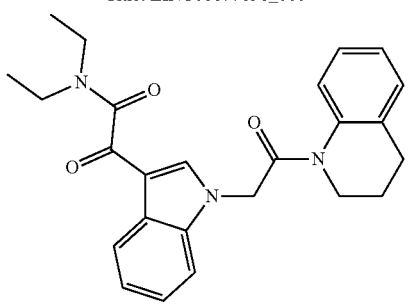
Title: ZINC02875406_000
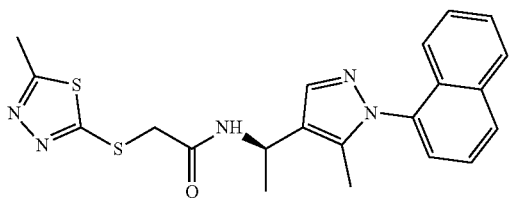
Title: ZINC12716857_000
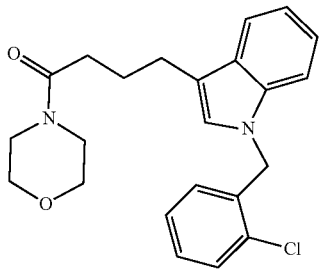
Title: ZINC09406314_000

33
-continued
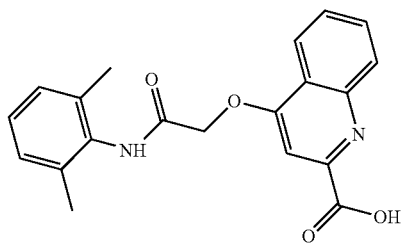
Title: ZINC15829528_000
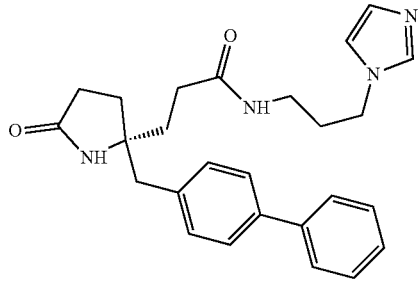
Title: ZINC11788776_000
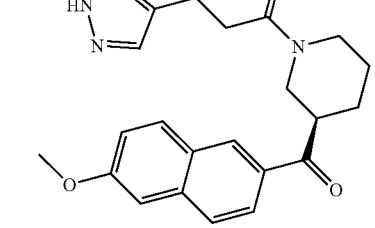
Title: ZINC12205348_000
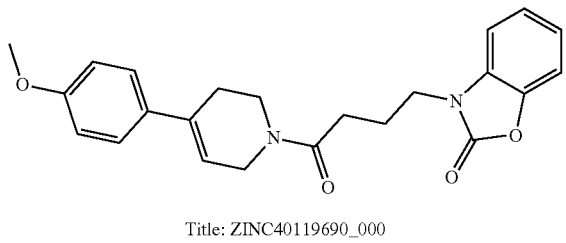
Title: ZINC40119690_000
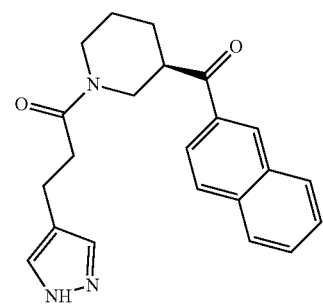
Title: ZINC11952630_000
34
-continued
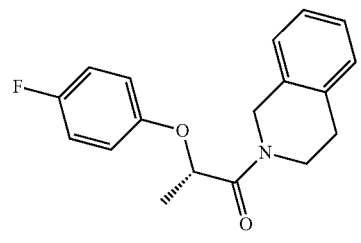
Title: ZINC12380537_000
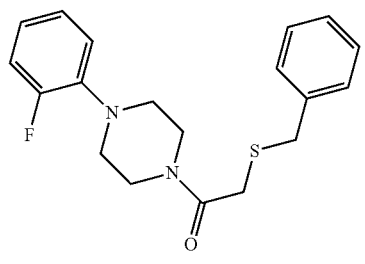
Title: ZINC00269748_000
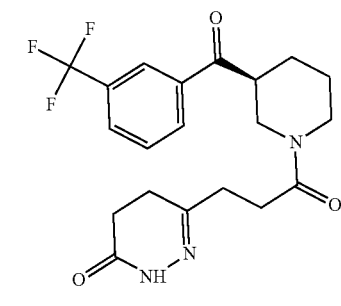
Title: ZINC12585926_000
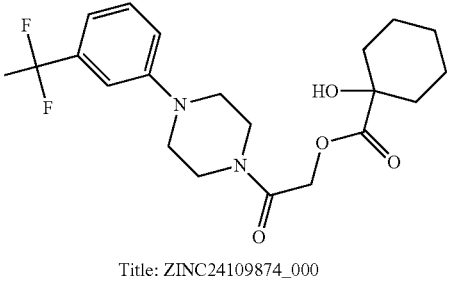
Title: ZINC24109874_000
Title: ZINC33268270_000
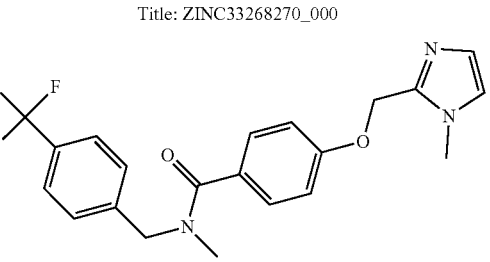
Title: ZINC44851466_000

35
-continued
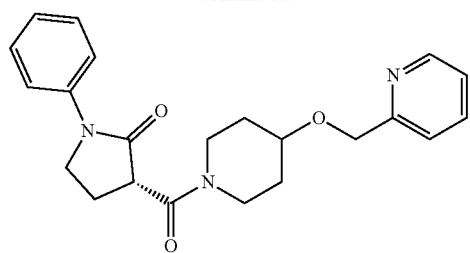
Title: ZINC12308533_000
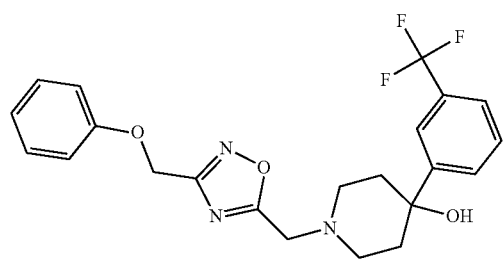
Title: ZINC14962091_000
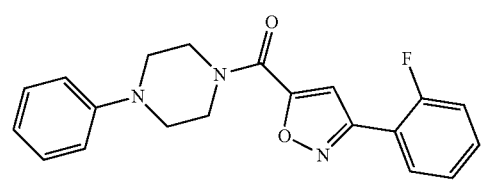
Title: ZINC06783109_000
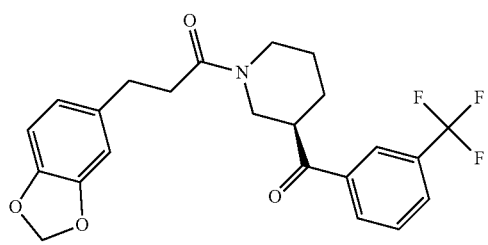
Title: ZINC14959559_000
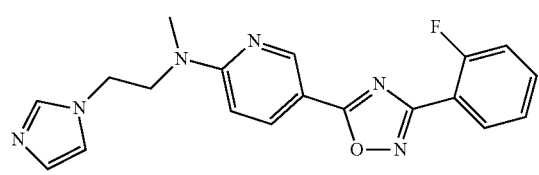
Title: ZINC15074732_000
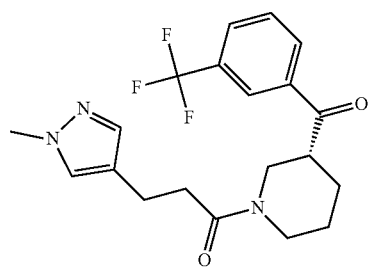
Title: ZINC12201323_000
36
-continued
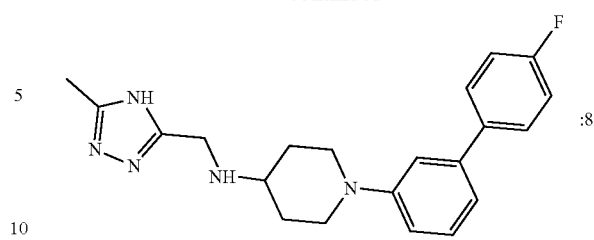
Title: ZINC20601040_000
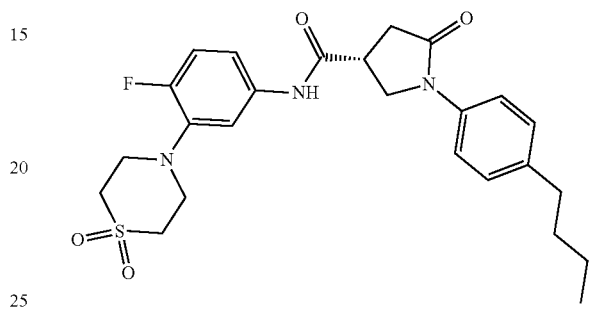
Title: ZINC40151772_000
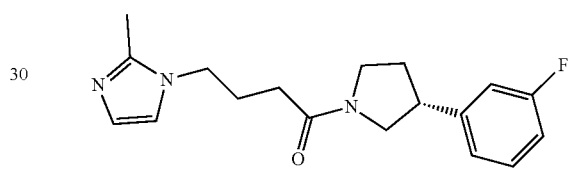
Title: ZINC69918342_000
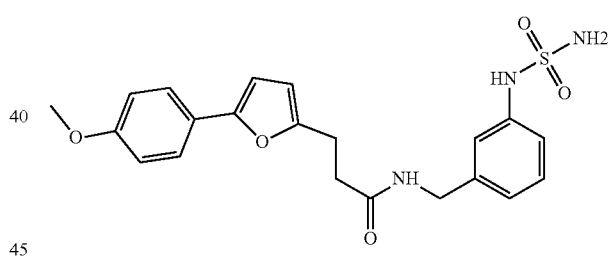
Title: ZINC32754061_000
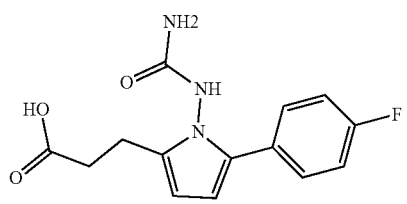
Title: ZINC02621723_000
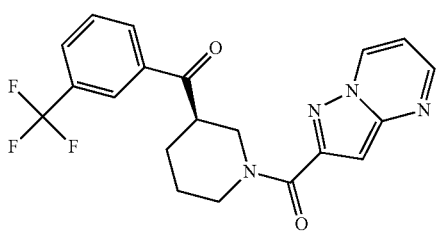
Title: ZINC12053851_000

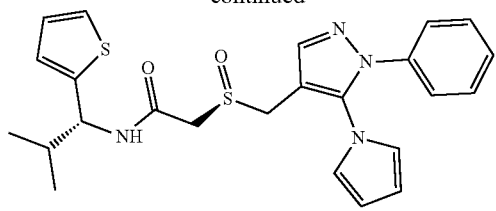

Title: ZINC21651128_000

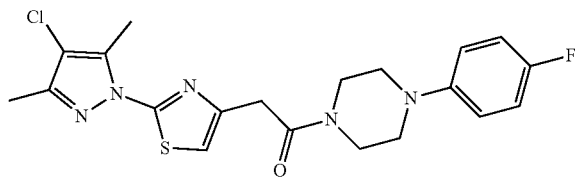

Title: ZINC33004440_000

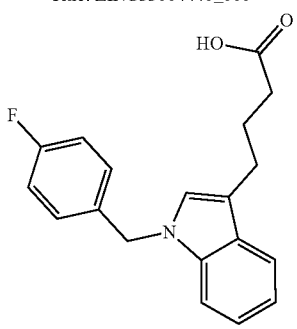

Title: ZINC06751208_000

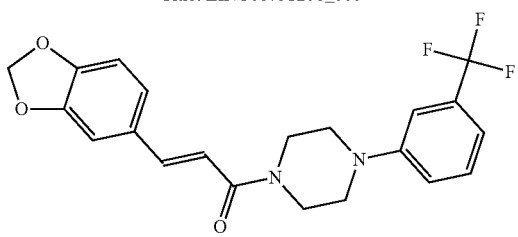

Title: ZINC01138331_000

Malignant melanoma is the most lethal form of skin cancer, which accounts from almost 80% of deaths related to skin cancer. There have been very little advances in the strategies for its management since past two decades. About 60% of melanoma has mutation in BRAF oncogene at V600E. These melanomas are also highly dependent on this constitutive activation of BRAF. Therefore, there was a recently approval of a BRAF (V600E) inhibitor vemurafenib. Although it was very effective tumor regression and improved patient survival, most of the patient suffered from frequent relapses of tumor formation due to drug resistance, which is a major setback of vemurafenib. The mechanism of resistance to vemurafenib is still unknown and widely being investigated. As shown hereinabove, up-regulation of Mcl-1 upon vemurafenib treatment as a potential mechanism of its resistance. Mcl-1 is upregulated during single as well as chronic treatment of vemurafenib in melanoma cells. Our results have also shown combination of vemurafenib with a Mcl-1 inhibitor overcome vemurafenib cell line. Hence, combination of vemurafenib with Mcl-1 inhibitors will prevent as well as overcome the resistance of melanoma cells to vemurafenib. Moreover, FDA recently approved a combination of BRAF inhibitor (Dabrafenib) and MEK 1/2 inhibitor (Trametinib). We have also observed similar Mcl-1 overexpression with either the single treatment with one of these inhibitors of its combination. Moreover, these inhibitors had very little effect on the cells overexpressing Mcl-1. Therefore, it is very important to include an Mcl-1 inhibitor to any therapy with a MAPK inhibitor and more importantly BRAF inhibitor. Novel inhibitors of Mcl-1 will be helpful in overcoming resistance to BRAF inhibitor therapy.

The present invention overcomes the very limited options available to manage malignant melanoma. There has been stagnancy in development of therapies to effectively manage this deadly disease. Approval of vemurafenib was a breakthrough in treating late stage malignant melanoma. However, resistance to vemurafenib has been a very big setback. It has not only limited the use of this drug but also thwarted the treatment of melanoma. However, approval of combination of BRAF inhibitor (Dabrafenib) and MEK 1/2 inhibitor (Trametinib) has given some hope for melanoma treatment. However, we have observed significant upregulation of Mcl-1 with the combination treatment or with a single agent treatment. These results showing the role of Mcl-1 up-regulation in MAPK inhibitor resistance can be utilize to prevent and overcome the resistance. Combination of BRAF inhibitor and MEK 1/2 inhibitor with Mcl-1 inhibitor will not only prevent the cells to become resistant to the treatment but also revert back the acquired resistance. This combination can be used for effective management of metastatic melanoma and other cancers.

Being highly specific, Mcl-1 inhibitors of the present invention can be used to treat any type of cancers expressing Mcl-1 irrespective of BRAF mutation and MAPK activation. Further, the Mcl-1 inhibitors taught herein can be used in combination with any other chemodrugs, treatment of which induces Mcl-1, irrespective of BRAF and MAPK pathway.

By establishing a proposed mechanism by which melanoma cells acquire resistance to BRAF inhibitor+MEK 1/2 inhibitor, the present inventors have identified novel, specific inhibitors of Mcl-1. Vemurafenib resistance has shown to have very devastating effects in melanoma patients and has limited its usage. The present invention demonstrates that increases in Mcl-1 provided resistance to vemurafenib in melanoma cells. The combination of vemurafenib with an Mcl-1 inhibitor not only had improved efficacy in wild type melanoma cells but also sensitized the resistant cells to vemurafenib treatment. Moreover, it was found that upregulation of Mcl-1 with Dabrafenib or Trametinib treatment led to tumor resistance. This is the first time where involvement of Mcl-1 induction upon Dabrafenib+Trametinib treatment has been reported. As an outcome of this study, BRAF+ MEK inhibitor in combination with Mcl-1 inhibitor can be used to effectively treat melanoma harboring mutant BRAF (V600E). Thus, Mcl-1 inhibitors can also be used to treat melanomas that do not possess mutant BRAF.

This study identifies the mechanism by which melanoma cells are resistant to BRAF inhibitor treatment. Mcl-1 is a very important anti-apoptotic protein, which has been constitutively activated in several cancers. It was very interesting to observe significant up-regulation of Mcl-1 in the cells that were treated with dabrafenib or trametinib treatment and these results prove the involvement of Mcl-1 in dabrafenib+ trametinib resistance. Hence, this study provides a novel drug combination which would not only overcome BRAF inhibitor resistance but also improve overall treatment of late stage malignant melanoma. By way of example, and in no way a limitation to the present invention, this study further shows that overexpression of Mcl-1 may be a mechanism of resistance to any of the inhibitors targeting MAPK.

This study shows, for the first, the involvement of Mcl-1 in BRAF+MEK 1/2 inhibitor resistance which is a problem when treating malignant melanoma with mutant BRAF. Using a combination of a BRAF inhibitor and an Mcl-1 inhibitor, it was found that therapy was improved against malignant melanoma but also against acquired resistance to BRAF+MEK inhibitor (Dabrafenib+Trametinib). The present invention includes the identification of Mcl-1 as being involved in drug resistance, and further teaches novel inhibitors of Mcl-1 that can be used to overcome resistance to BRAF inhibitors or in combination with MEK inhibitor in cancer.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention claimed is:

1. A composition for inhibiting melanoma growth or reducing the size of a solid tumor that is melanoma or extending the life span of a subject that has melanoma or inducing apoptosis of melanoma cells, the composition comprising:

at least one of a MAPK pathway protein, a mutant MAPK pathway protein, or a MAPK pathway protein kinase; and
an Mcl-1 inhibitor selected from at least one of:
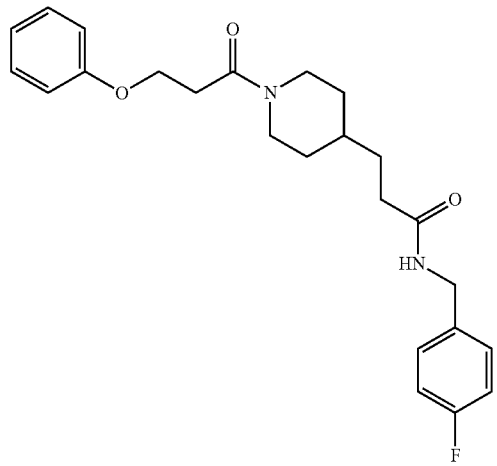
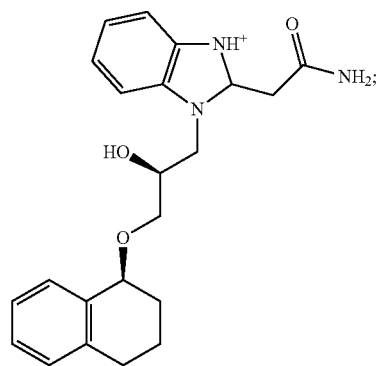
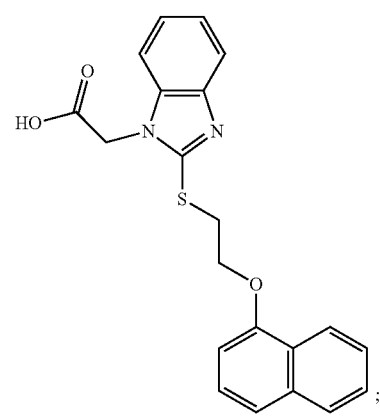
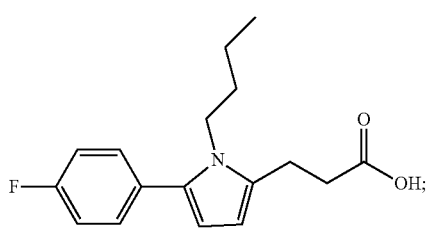
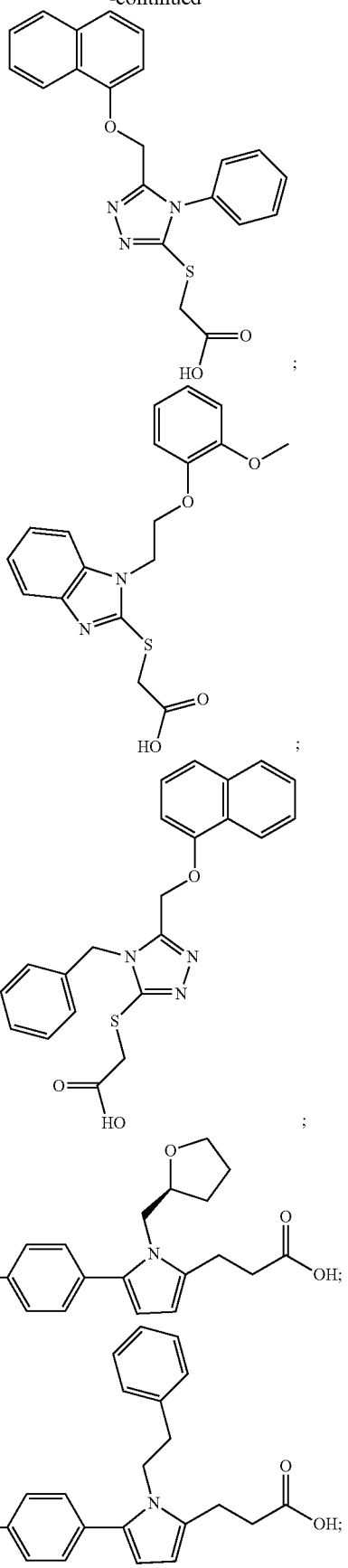

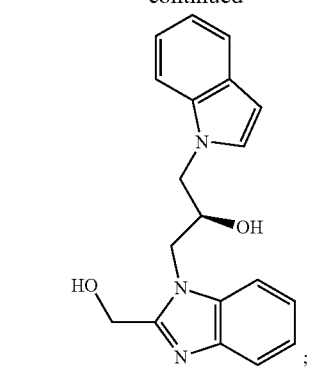
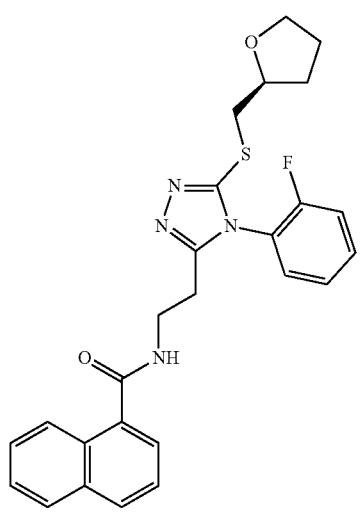
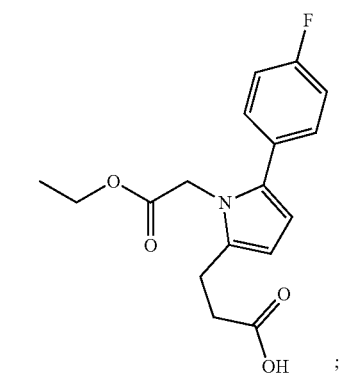
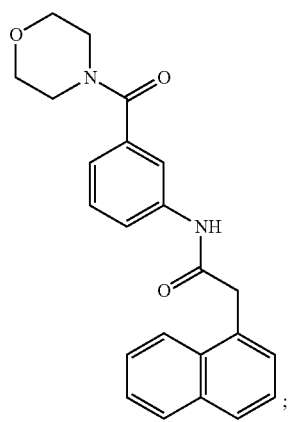
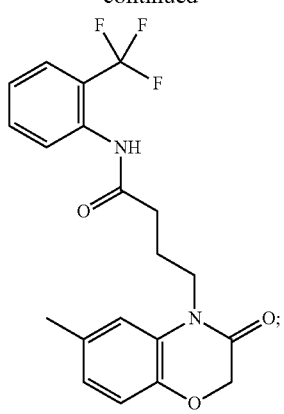
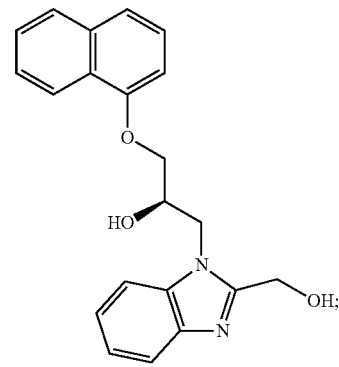
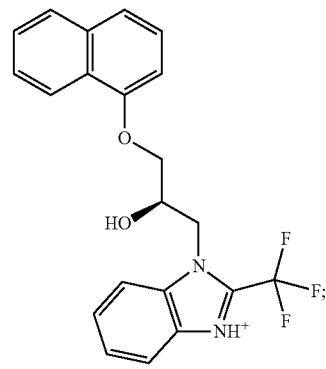
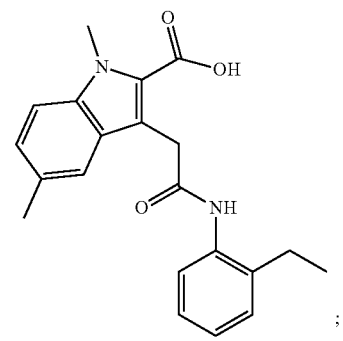

45
-continued
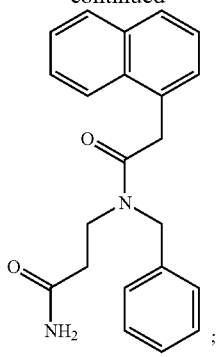
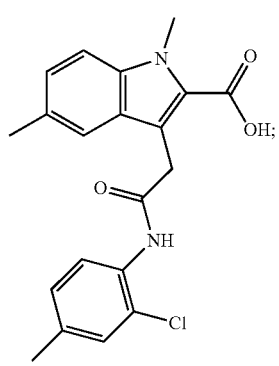
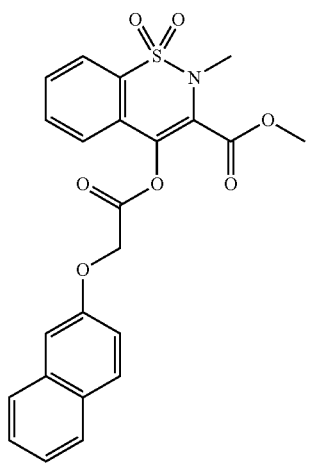
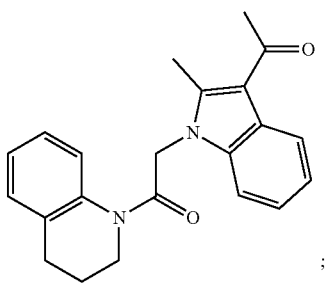
46
-continued
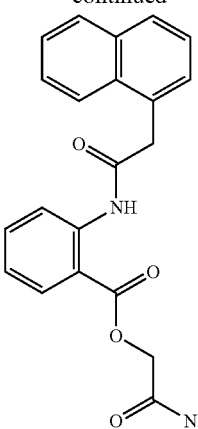
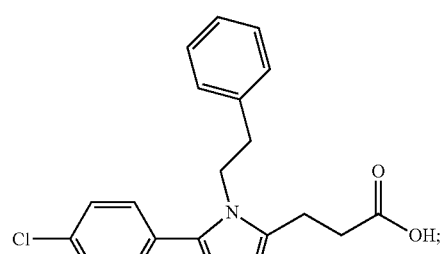
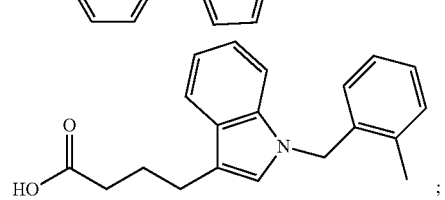
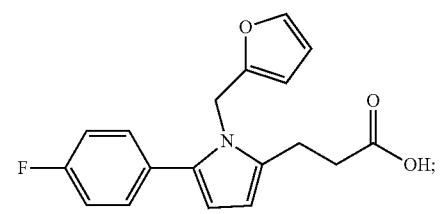
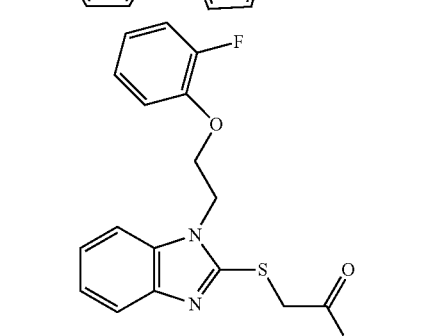
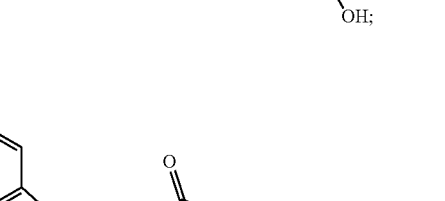
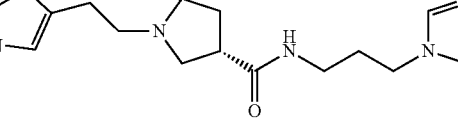

47
-continued
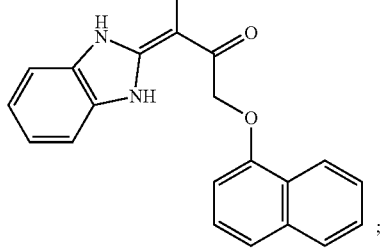
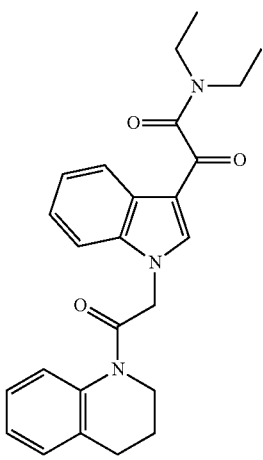
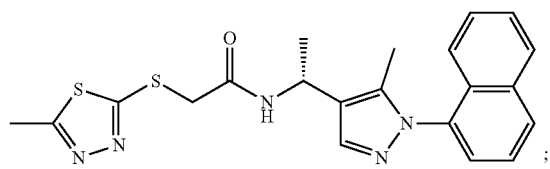
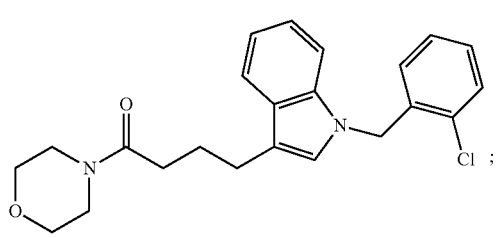
48
-continued
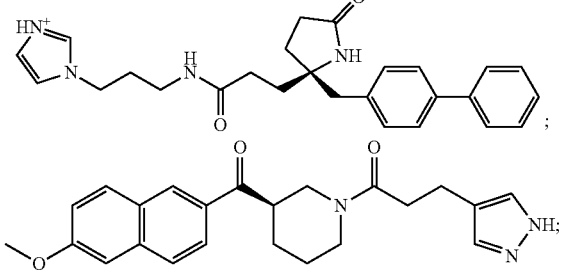
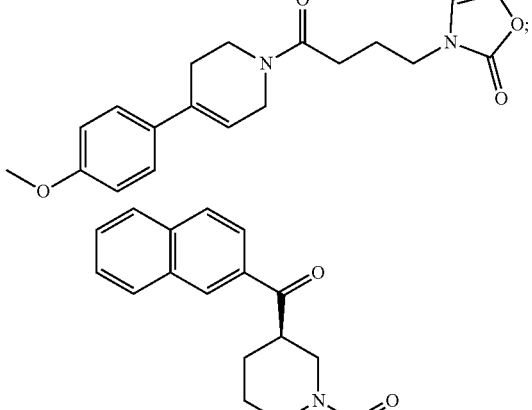
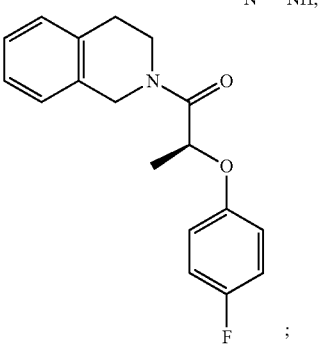

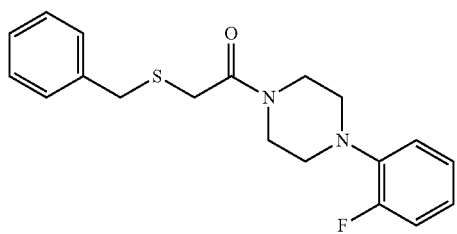
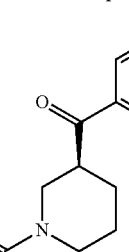
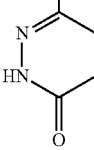
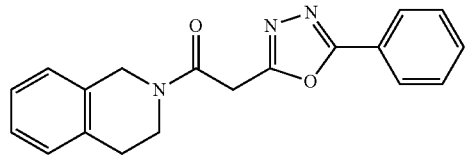
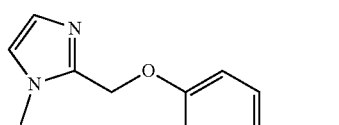
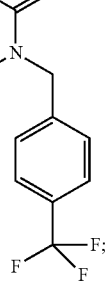
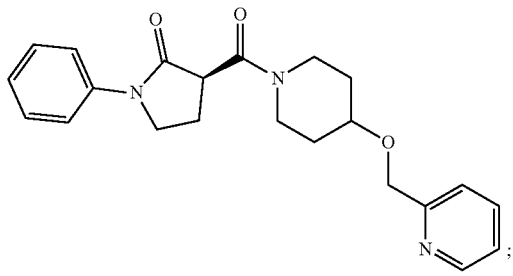
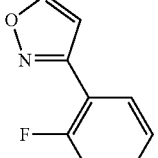

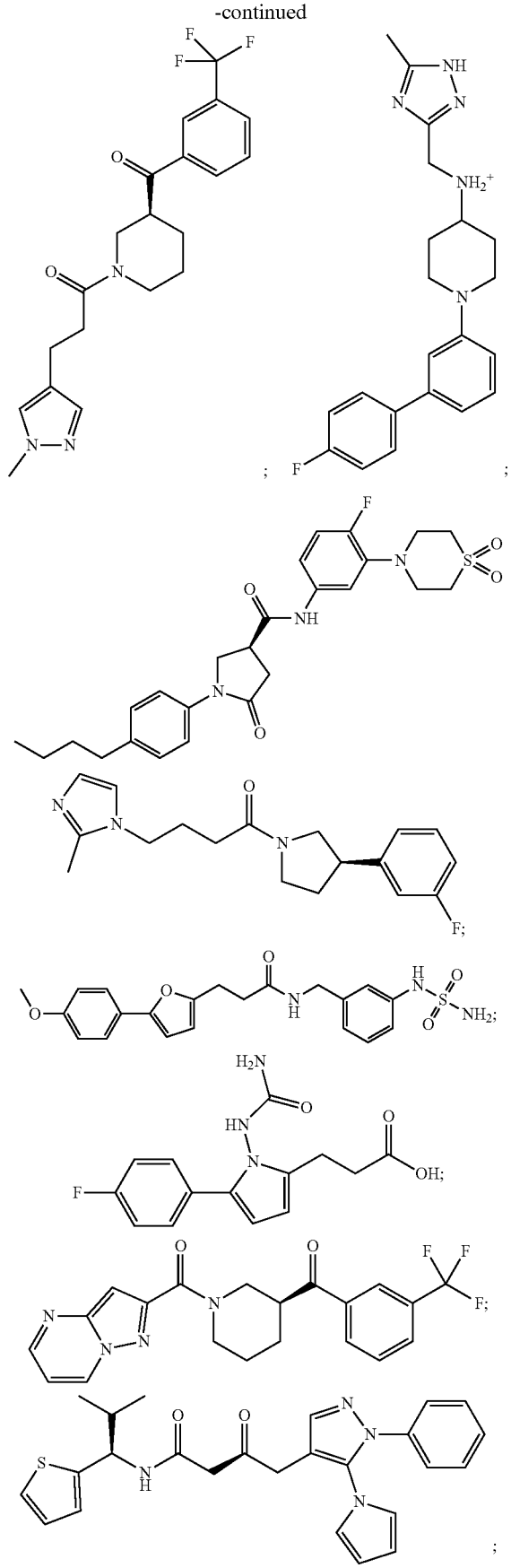

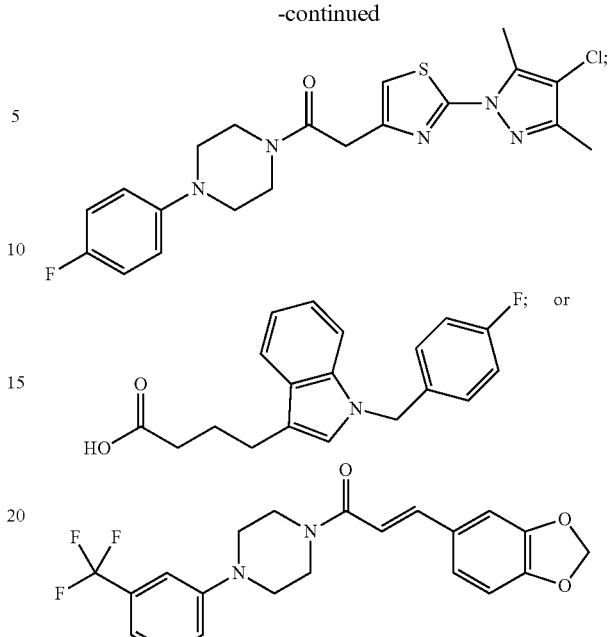

2. The composition of claim 1, wherein the MAPK pathway protein is selected from at least one of wild type or mutated BRAF, CRAF, MEK 1, MEK 2, ERK1, ERK2, NRAS, and KRAS.

3. The composition of claim 1, further comprising one or more Mcl-1 inhibitors selected from at least one of an antibody that blocks Mcl-1 activity, omacetaxine mepesuccinate, 2-(R)-(1-Ethyl-2-hydroxyethylamino)-6-benzylamino-9-isopropylpurine (Seliciclib), a small interfering RNA (siRNA) or a small hairpin RNA (shRNA) that inhibits expression of Mcl-1, antagonists of Mcl-1 isotype 1, agonists of Mcl-1 isotype 2, benzylisothiocyanate, phenethylisothiocyanate, diindolyl methane, curcumin, piperlongumine, Marinopyrrole A, Cucurbitacin B, Capsaicin, Penfluridol, Perphenazine, Bcl-2 inhibitors, Bcl-2 siRNA/shRNA, Bcl-XL inhibitors, Bcl-XL siRNA/shRNA and any other Bcl-2 family inhibitors, a small interfering RNA (siRNA) that inhibits expression of Mcl-1, or a salt thereof.

4. The composition of claim 1, wherein the MAPK pathway protein or kinase inhibitor is selected from at least one of GDC-0879, PLX-4720, Sorafenib Tosylate, Dabrafenib, Trametinib, LGX818, Vemurafenib, or a salt thereof.

5. The composition of claim 1, further comprising one or more other anti-cancer agents.

6. The composition of claim 1, wherein the cells of the tumors or tumor metastases are relatively insensitive or refractory to treatment with the inhibitor of the MAPK pathway protein, the mutant MAPK pathway protein, or the MAPK pathway protein kinase as a single agent.

7. The composition of claim 1, wherein the MAPK pathway protein is a wild type or a mutated BRAF and the inhibitor of the BRAF is a small interfering RNA (siRNA) that inhibits expression of BRAF or a small molecule that reduces the overall BRAF activity in a cell.

8. The composition of claim 1, wherein the tumor is insensitive to the inhibitor of the MAPK pathway protein, the mutant MAPK pathway protein, or the MAPK pathway protein kinase administered alone.

9. The composition of claim 1, wherein the tumor that overexpresses Mcl-1 is a primary tumor, or a tumor metastasis.

\* \* \* \* \*